United States Patent [19]

Dillner et al.

[11] Patent Number: 5,180,806
[45] Date of Patent: Jan. 19, 1993

[54] POLYPEPTIDES AND COMPOSITIONS OF HUMAN PAPILLOMAVIRUS LATENT PROTEINS, DIAGNOSTIC SYSTEMS AND METHODS

[75] Inventors: Joakim Dillner, Stockholm, Sweden; Richard A. Lerner, La Jolla, Calif.; Richard Smith; D. Elliot Parks, both of Del Mar, Calif.

[73] Assignee: The Scripps Research Institute, La Jolla, Calif.

[21] Appl. No.: 323,614

[22] Filed: Mar. 13, 1989

Related U.S. Application Data

[63] Continuation-in-part of Ser. No. 194,407, May 16, 1988, abandoned.

[51] Int. Cl.$^5$ .............. A61K 37/02; C07K 5/00; C07K 7/00; C07K 15/00
[52] U.S. Cl. .................. 530/326; 530/324; 530/325
[58] Field of Search ............. 530/324, 325, 326

[56] References Cited

U.S. PATENT DOCUMENTS 4,748,109  5/1988  Baird .
4,777,239  10/1988  Schoolnik et al. .................. 530/326

FOREIGN PATENT DOCUMENTS 0257754  3/1988  European Pat. Off. .
8600629  10/1988  PCT Int'l Appl. .

OTHER PUBLICATIONS

Seedorf et al.; Virology, vol. 145, pp. 181–185, 1985.
Dillner et al., PNAS, vol. 86, pp. 3838–3841, 1989.
Peptide Hormones, Rudinger, Univ. Park Press, Baltimore, J. Parsons Edit., 1976 pp. 1–7.
Cason et al., J. Gen. Virol., vol. 70, pp. 2973–2987, 1989.
Androphy, *EMBO. J.*, 6:989–992 (1987).
Banks, et al., *J. Gen. Virol.*, 68: 1351–1359 (1987).
Banks, et al., *J. Gen. Virol.*, 68: 3081–3089 (1987).
Cole, et al., *J. Mol. Biol.*, 193: 599–608 (1987).
Danos, et al., *Cancer Cells*, 5: 145–149 (1987).
Doorbar, et al., *Virology*, 172: 51–62 (1989).
Firzlaff, et al., *Cancer Cells*, 5: 105–113 (1987).
Gissmann, et al., *Cancer Cells*, 5: 275–280 (1987).
Jenison, et al., *J. Virol.*, 62: 2115–2123 (1988).
Larsen, et al., *Cancer Cells*, 5: 319–327 (1987).
Lehn, et al., *J. Gen. Virol.*, 65: 2003–2010 (1984).
Li, et al., *J. Virol.*, 62: 606–609 (1988).
Mallon, et al., *J. Virol.*, 61: 1655–1660 (1987).
Oltersdorf, et al., *J. Gen. Virol.*, 68: 2933–2938 (1987).
Seedorf, et al., *EMBO J.*, 139–144 (1987).
Smotkin, et al., *Proc. Natl. Acad. Sci., U.S.A.*, 83: 4680–4684 (1986).
Spence, *Cancer Res.*, 48: 324–328 (1988).

*Primary Examiner*—Merrell C. Cashion, Jr.
*Assistant Examiner*—A. M. Davenport
*Attorney, Agent, or Firm*—Douglas A. Bingham; Thomas Fitting; April C. Logan

[57] ABSTRACT

The present invention relates to polypeptides that immunologically mimic papillomavirus latent proteins and to antibodies and monoclonal antibodies that immunoreact with papillomavirus latent proteins. Systems and methods for detecting the presence and type of papillomavirus in a human subject are also described.

7 Claims, 5 Drawing Sheets

POLYPEPTIDES AND COMPOSITIONS OF HUMAN PAPILLOMAVIRUS LATENT PROTEINS, DIAGNOSTIC SYSTEMS AND METHODS

CROSS REFERENCE TO RELATED APPLICATION

This is a continuation-in-part application of copending application Ser. No. 194,407, filed May 16, 1988 and now abandoned, the disclosures of which are herein incorporated by reference.

DESCRIPTION

1. Technical Field

The present invention relates to antibody and monoclonal antibody compositions containing antibody molecules that immunoreact with latent papillomavirus (PV) proteins. The present invention also relates to methods of preparing these antibody molecules and to methods of detecting these latent PV proteins and latent PV infection.

2. Background

Papillomaviruses induce benign, dysplastic and malignant hyperproliferations of skin or mucosal epithelium. Pfister, *Rev. Physiol. Biochem. Pharmacol.*, 99:111-181 (1984). According to Nuovo et al., *J. Virol*, 62:1452-1455 (1988) 51 types (strains) of human papillomavirus (HPV) have been identified.

In humans, different papillomavirus types are known to cause distinct diseases, Pfister, *Adv. Cancer Res.*, 48:113-147 (1987), Syrjanen, *Obstet. Gynecol. Survey*, 39:252-265 (1984). For example, human papillomavirus (HPV) types 1 and 2 cause common warts, and types 6 and 11 cause condylomas and genital flat warts. In contrast, HPV types 16, 18 and 33 are carried in a majority of cervical cancers and do not cause the usual condyloma but rather persist diffusely in the cervical endothelium exhibiting only minimal pathologic changes. It is believed that the HPV types associated with cervical cancer are maintained in a latent state in cervical endothelium tissues for years after initial infection and then progress in some cases to cause cervical cancer.

The genome of many of the presently identified HPV types has been cloned and sequenced. See, for example, Baker, "Sequence Analysis of Papillomavirus Genomes", in *The Papovaviridae-Volume 2: The Papillomaviruses*, Salzman et al., eds., Plenum Press, New York, pp. 321-386 (1987); and Chow et al., *Cancer Cells*, 5:55-72 (1987).

Historically, the open reading frames (ORFs) of papillomavirus genomes have been designated L1 and L2 and E1 to E7, where "L" and "E" denote late and early, respectively. L1, L2 and E4 code for viral capsid proteins and E region ORFs are thought to be associated with functions such as viral replication, transformation and plasmid maintenance. Howley et al., "Molecular Aspects of Papillomavirus-Host Cell Interactions", in *Viral Etiology of Cervical Cancer*, Peto et al., eds., Banrury Report 21, Cold Spring Harbor Laboratory, pp. 261-272 (1986); and Doorbar et al., *EMBO J.*, 5:355-362 (1986).

Presently, there are no papillomavirus-specific antigens that have been unambiguously identified as being either expressed during, or indicative of, latent HPV infection.

This is in contrast to HPV infected tissues where there are actively replicating viruses. In those tissues the presence of some HPV-encoded replication-related antigens (e.g., viral capsid antigen) has been demonstrated. Schneider, "Methods of Identification of Human Papillomaviruses," in *Papillomaviruses and Human Disease*, Syrjanen et al., eds., Springer-Verlag, pp. 19-39 (1987).

Several studies have reported attempts to identify the protein products of HPV-containing cell lines. Fusion proteins were expressed in *Escherichia coli* in which various HPV ORF region nucleotide sequences were operatively linked to heterologous genes. The resulting fusion protein product contained a non-HPV amino terminus and part or all of the putative ORF-encoded amino acid residues at the carboxy terminus. The expressed fusion protein was used as an immunogen to raise polyclonal antisera, and the sera was then used to detect putative HPV-encoded proteins in vitro in HPV-containing cell lines.

For instance, Seedorf et al., *EMBO J.*, 6:139-144 (1987) raised antibodies to a fusion protein containing E1 ORF sequences and detected a 70 kilodalton (kd) protein after in vitro translation of mRNA isolated from HeLa cells containing HPV type 18. Using antisera raised against a fusion protein containing E4 ORF sequences, a 10 kd protein was detected by in vitro translation of mRNA from HPV type 16-containing CaSki cells. Seedorf et al., *EMBO J.*, 6:139-144 (1987). Similarly, antisera directed against an E6 ORF sequence-derived fusion protein detected an 11 kd protein by in vitro translation of mRNA from HPV type 16-containing CaSki cells. Seedorf et al., *EMBO J.*, 6:139-144 (1987).

Antisera raised to various fusion proteins that contained E7 ORF sequences have detected several proteins depending on the HPV type studied. In HPV 16 infected cells, a 15 kd protein has been detected using Western immunoblotting and radioimmuno-precipitation methodologies using CaSki or SiHa cells as the HPV source. Seedorf et al., *EMBO J.*, 6:139-144 (1987); and Firzlaff et al., *Cancer Cells*, 5:105-113 (1987). Smotkin et al., [*Proc. Natl. Acad. Sci. USA*, 83:4680-4684 (1987)] have described using antibodies raised against an E7 ORF sequence-derived fusion protein to detect a 20 kd protein by immunoprecipitation of HPV type 16-containing CaSki or SiHa cells.

Monoclonal antibodies have been prepared against an E7 ORF-containing fusion protein that detect a 15 kd protein in HPV 16-containing cells by using both Western and immunoprecipitation methodologies. Oltersdorf et al., *J. Gen. Virol.*, 68:2933-2938 (1987).

Recently, Li et al., [*J. Gen Virol.*, 62:606-609 (1988)] described an antisera raised against an E2 ORF containing fusion protein which was used to detect proteins present in primary biopsy tissues known to contain HPV genomic sequences. A 50 kd protein was detected by Western immunoblotting of lysates from several tissues diagnosed as condylomas and demonstrated by Southern blotting to contain HPV types 6, 11 or 16.

By way of further background, seventeen synthetic polypeptides have been described whose amino acid residue sequences correspond to portions of the HPV. type 16 E1, E2, E4, E6, or E7 ORFs, or to a portion of the E6 ORF region of HPV type 6. Schoolnick et al., EPO patent application no. 0257754A2, published Mar. 2, 1988. These polypeptides were used as immunogens to prepare rabbit antisera, and four of the prepared anti-peptide antibodies raised against an E6 region of HPV-16 were shown to immunoreact with patient biopsy tissue shown to contain HPV-16 DNA and that were assessed as having known dysplasias. However, none of the Schoolnik et al. peptides was demonstrated as having the ability to react as an antigen with antibodies induced as a result of HPV infection.

BRIEF DESCRIPTION OF THE INVENTION

The present invention contemplates a polypeptide represented by a formula selected from the group consisting of:

MADPAGTNGEEGTGC,

HEDEDKENDGDSLPTC,

RPFKSNKSTCC,

CCDWCIAAFGLTPSI,

TYDSEWQRDQFLSQVKIPC,

HKSAIVTLTYDSEWQRDQC, and

CINCQKPLCPEEKQRH.

Further contemplated is a polypeptide comprising no more than about 50 amino acid residues and including an amino acid residue sequence having the formula:

—TYDSE—.

Another embodiment contemplates a polypeptide comprising no more than about 50 amino acid residues and including an amino acid residue sequence represented by the formula selected from the group consisting of:

—TGILTVTYHSE—,
—HAIVTVTYDSE—,
—NAIVTLTYSSE—,
NGIVTVTFUTE—, and
—ILTVT—.

Also contemplated is a composition comprising a substantially pure human papillomavirus 54 kd filamentous protein, said protein containing a first epitope having the capacity to immunoreact with anti-polypeptide antibodies induced by a polypeptide represented by the formula:

MADPAGTNGEEGTGC;

and containing a second epitope having the capacity to immunoreact with anti-polypeptide antibodies induced by a polypeptide represented by the formula:

CINCQKPLCPEEKQRH.

Further contemplated is a composition comprising a substantially pure human papillomavirus 48 kd filamentous protein, said protein containing a first epitope having the capacity to immunoreact with anti-polypeptide antibodies induced by a polypeptide represented by the formula:

MADPAGTNGEEGTGC;

and containing a second epitope having the capacity to immunoreact with anti-polypeptide antibodies induced by a polypeptide represented by the formula:

CINCQKPLCPEEKQRH.

Another aspect is composition comprising a substantially pure human papillomavirus 112 kd diffuse protein, said protein containing a first epitope having the capacity to immunoreact with anti-peptide antibodies induced by a polypeptide represented by the formula:

HEDEDKENDGDSLPTC;

and containing a second epitope having the capacity to immunoreact with anti-polypeptide antibodies induced by a polypeptide represented by the formula:

HKSAIVTLTYDSEWQRDQC.

A further aspect is a composition comprising a substantially pure human papillomavirus 51 kd nuclear protein, said protein containing an epitope having the capacity to immunoreact with anti-peptide antibodies induced by a polypeptide represented by the formula:

HKSAIVTLTYDSEWQRDQC.

Also contemplated is an anti-polypeptide antibody that immunoreacts with only one of the polypeptides selected from the group consisting of:

MADPAGTNGEEGTGC,

HEDEDKENDGDSLPTC,

RPFKSNKSTCC,

CCDWCIAAFGLTPSI,

TYDSEWQRDQFLSQVKIPC,

HKSAIVTLTYDSEWQRDQC, and

CINCQKPLCPEEKQRH.

Further contemplated is a monoclonal antibody containing antibody molecules that immunoreact with a human papillomavirus latent protein selected from the group consisting of:
  i) the 112 kd diffuse protein,
  ii) the 54 kd filamentous protein,
  iii) the 48 kd filamentous protein,
  iv) the 51 kd nuclear protein; and
  v) the 58 kd nuclear protein.

In another aspect the present intention contemplates an antibody containing substantially isolated or substantially pure antibody molecules that immunoreact with a human papillomavirus latent protein selected from the group consisting of:
  i) the 112 kd diffuse proten,
  ii) the 54 kd filamentous protein,
  iii) the 48 kd filamentous protein,
  iv) the 51 kd nuclear protein; and
  v) the 58 kd nuclear protein.

Further contemplated are antibody and monoclonal antibody molecules that immunoreact with the polypeptides of the present invention, in addition to compositions containing the contemplated polypeptides or contemplated antibody molecules.

Diagnostic systems, in kit form, containing, is an amount sufficient to perform at least one assay, one or more of the above described polypeptides, protein compositions and antibodies are also contemplated.

Methods for assaying for the presence of papillomavirus infection and type of papillomavirus present using the above described polypeptides, protein compositions and antibodies are further contemplated.

| ORF | Nucleotide Sequence Included |
|-----|------------------------------|
| E6  | 65-556    |
| E7  | 544-855   |
| E1a | 859-1167  |
| E1b | 1104-2810 |
| E2  | 2725-3849 |
| E4  | 3332-3616 |
| E5  | 3862-4096 |
| L2  | 4133-5653 |
| L1  | 5526-7151 |

The translational phase of the ORF is indicated by the "R" designation on the left wherein "R1" indicates phase 1, "R2" indicates phase 2 and "R3" indicates phase 3. A scale measured in nucleotide kilobases (kb) is located below the ORFs to indicate their relative positions.

Figure 2:
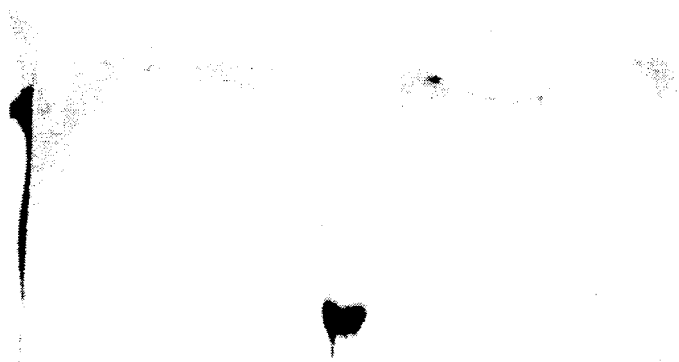
Figure 2:

FIG. 2 illustrates an immunoblot analysis of human papillomavirus latent proteins present in HPV-containing tissue cultures and biopsy tissue samples. Cell lysates were prepared, electrophoresed in 7.5% polyacrylamide gels and immunoblotted as described in Example 5 using rabbit anti-polypeptide 236 antisera.

Lanes 1 through 4 show the results obtained using cell lysates prepared from the cervical carcinoma cell lines CaSki, HeLa, SiHa and C-33a, respectively. This antisera immunoreacts with an 112 kilodalton (kd) protein present in HeLa and SiHa cells, and also immunoreacts non-specifically with a protein having a molecular weight of about 70,000 present in all cell lysates analyzed (lanes 1-4, 6, 7). Lane 5 contains the following protein standards electrophoresed as markers having the following molecular weights indicated in kd; lysozyme, 14.4 kd.; trypsin inhibitor, 21.5 kd; carbonic anhydrase, 31 kd; ovalbumin, 42.7 kd; bovine serum albumin, 66.2 kd; phosphorylase b, 97.4 kd; beta-galactosidase, 116.25; and myosin, 200 kd. Lanes 6 and 7 show the results obtained using cell lysates prepared from two different condyloma biopsy tissue samples. One condyloma biopsy lysate (lane 6) contains both the 54 kd and 46 kd filamentous proteins, whereas the other condyloma biopsy lysate contains only the 54 kd species.

Figure 3:
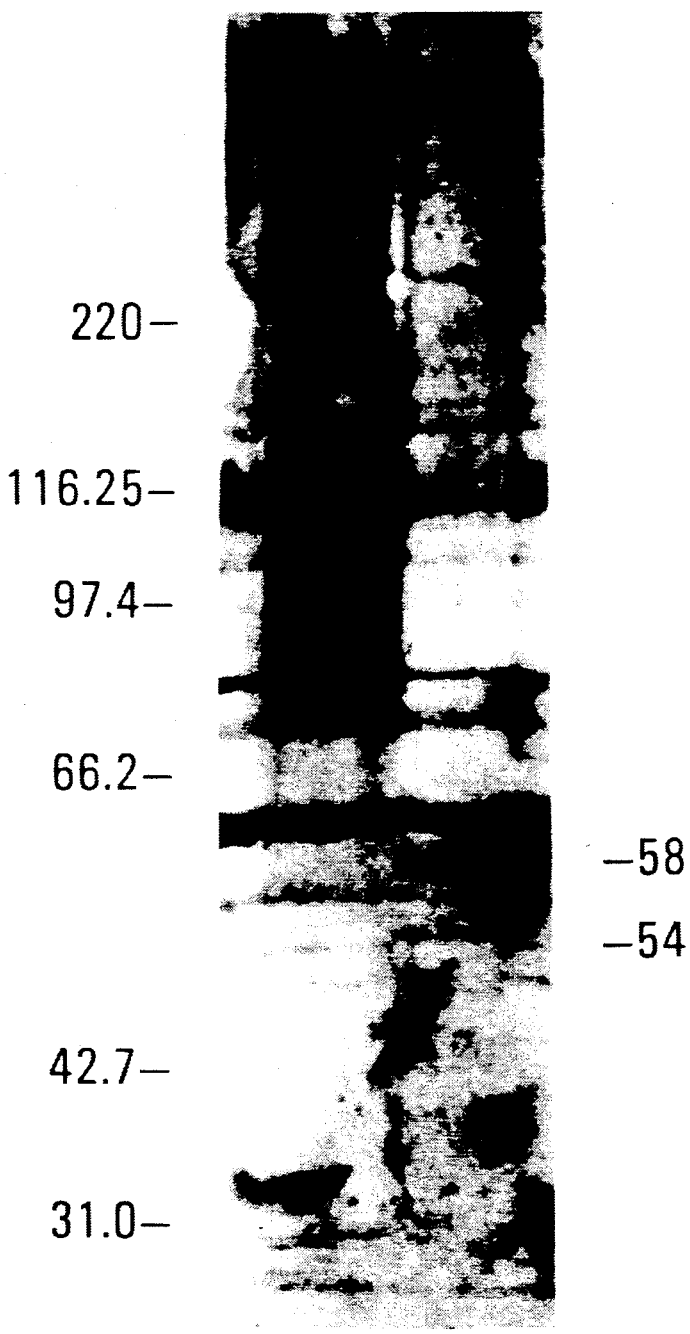

FIG. 3 illustrates a type-specific immmunoblot analysis of human papillomavirus latent proteins present in HPV-containing cervical carcinoma cells. Cell lysates were prepared, electrophoresed in 7.5% polyacrylamide gels and immunoblotted as described in Example 5 using rabbit anti-polypeptide 236 antisera. In addition to all the non-specific proteins detectable using the polyclonal antisera, the 58 kd and 54 kd filamentous proteins were detected in cell lysates prepared from CaSki cells (lane 2) but not in cell lysates prepared from HeLa cells (lane 1). Although not shown, the same molecular weight marker proteins as described for FIG. 2 were included on the immunoblot, which inclusion provided a means to determine the molecular weights of the observed proteins.

Figure 4:
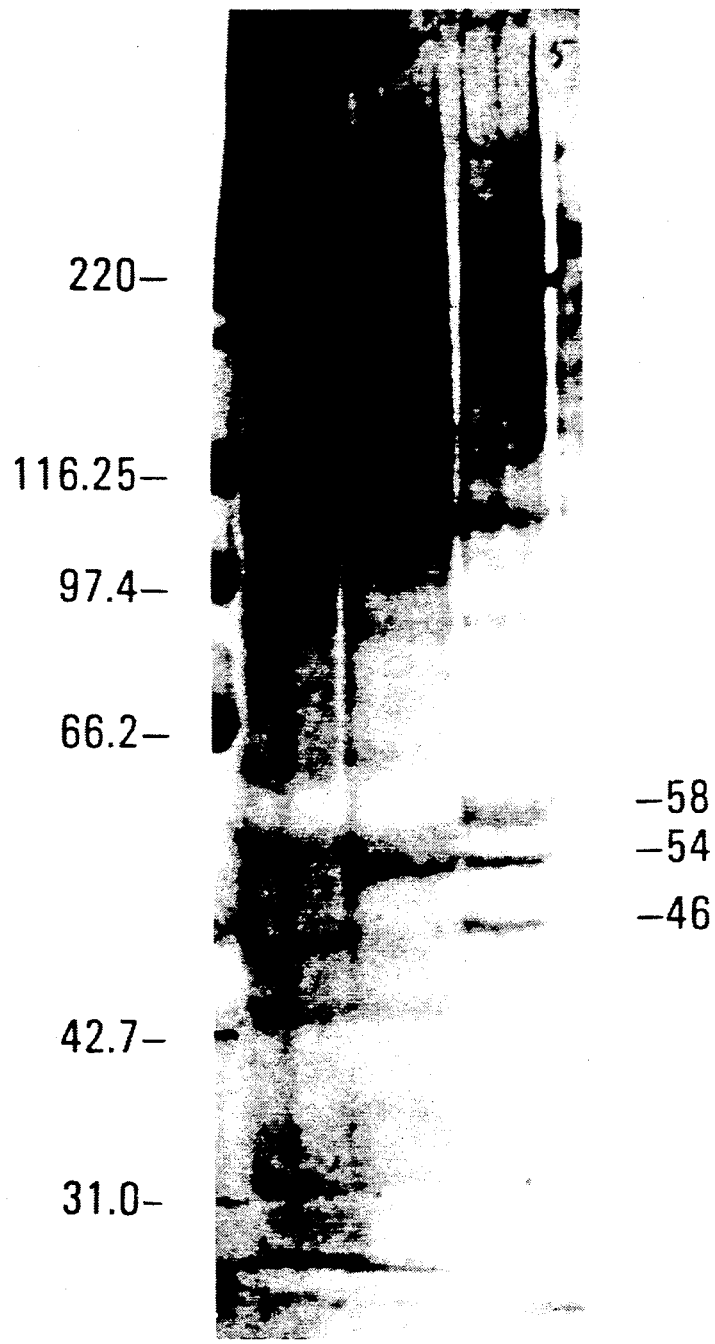

FIG. 4 illustrates an immunoblot analysis of human papillomavirus latent proteins present in HPV-containing cervical carcinoma cells. Cell lysates were prepared, electrophoresed in 7.5% polyacrylamide gels and immunoblotted as described in Example 7 using monoclonal antibody 247:4D11. Lane 1 contains the same molecular weight marker proteins as described in FIG. 2. Lanes 2 through 5 show the results obtained using cell lysates prepared from cervical carcinoma cell lines SiHa, HeLa, CaSki and HT-3, respectively. HPV latent proteins detected in CaSki cells include the 58 kd, 54 kd and 48 kd filamentous proteins (lane 4), whereas only the 54 kd protein was detected in HeLa cells. All the other proteins detected are nonspecific immunoreaction products observed when using monoclonal antibody 247:4D11.

Figure 5A:
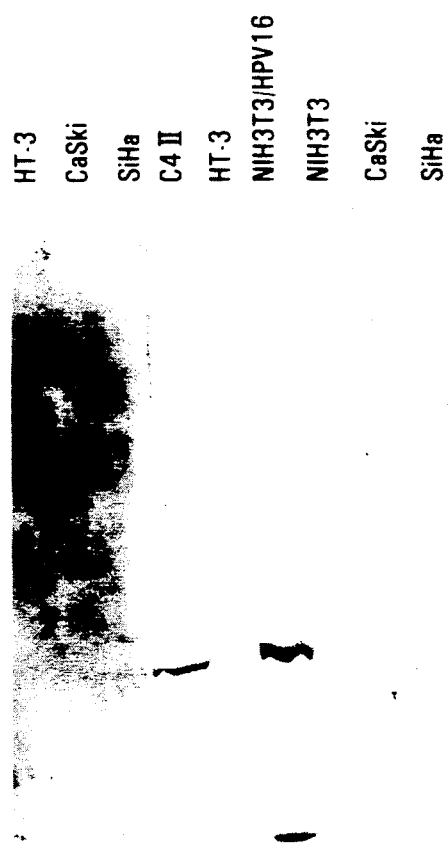
Figures 5B, 5C:
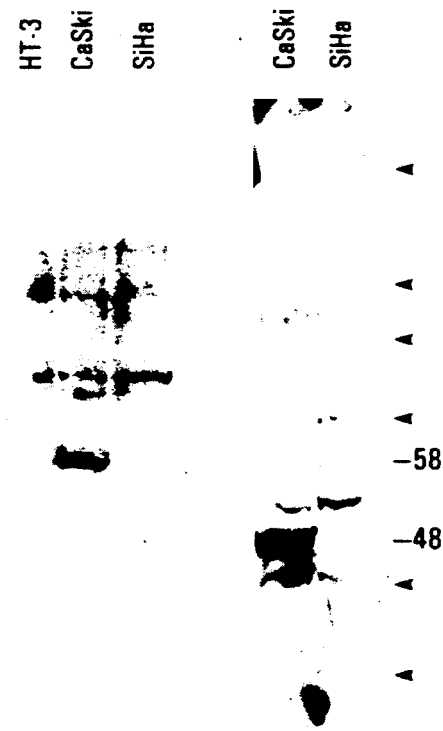

FIGS. 5A, 5B and 5C illustrate an immunoblot analysis of human papillomavirus latent proteins present in HPV-containing cervical carcinoma cells. Cell lysates were prepared, electrophoresed in 7% polyacrylamide gels and immunoblotted as described in Example 16a using human anti-HPV latent protein antibody molecules affinity isolated on polypeptide 245 (Panel 5A), hybridoma 245:11E3 culture supernatant (Panel 5B), or rabbit affinity isolated anti-polypeptide 245 antibody molecules (Panel 5C). Each cell lysate analyzed is listed at the top of its respective gel lane. Numerals at the right and left margins of the figure denote the molecular weight in kilodaltons (kd) of the major immunoreacting species, 58 kd and 48 kd. Arrowheads indicate the positions of the marker proteins having a molecular weight of 200, 116, 92, 66, 44 and 31 kd, respectively. The left part of Panel A and the entire Panel B were developed for 12 hours, whereas the right part of Panel A and the entire Panel C were developed for 30 minutes.

DETAILED DESCRIPTION OF THE INVENTION

A. Definitions

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Try | L-tryptophan |

-continued

TABLE OF CORRESPONDENCE

| SYMBOL | | |
|---|---|---|
| 1-Letter | 3-Letter | AMINO ACID |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a bond to a further sequence of one or more amino acid residues up to a total of about fifty residues in the polypeptide chain.

Polypeptide and Peptide: Polypeptide and peptide are terms used interchangeably herein to designate a linear series of no more than about 50 amino acid residues connected one to the other by peptide bonds between the alpha-amino and carboxy groups of adjacent residues.

Protein: Protein is a term used herein to designate a linear series of greater than 50 amino acid residues connected one to the other as in a polypeptide.

B. Papillomavirus Latent Proteins

Papillomavirus infections can result in the virus being maintained in the infected tissue in a latent state. As it is presently understood for human papilloma viruses (HPVs), viral latency occurs for those HPV types associated with genital papillomavirus infection, particularly those which cause various dysplasias such as cervical cancer. Dysplasia-associated HPV types include types 16, 18, 31 and 33, 35, 52 and the like.

Prior to the making of the present invention, the presence of papillomavirus genome E region ORF-encoded proteins had not been detected in papillomavirus-infected tissues that maintained the virus in a latent state. It is now demonstrated herein that papillomavirus specific proteins are expressed in infected tissues harboring the virus in a latent, non-replicative state.

Broadly, therefore, one embodiment of the present invention contemplates a papillomavirus latent protein in substantially pure form. As used herein, the phrases "papillomavirus latent protein," "latent papillomavirus protein" and the like refer to a protein encoded by a HPV E ORF that is expressed in tissue latently infected with HPV. Tissues latently infected with HPV contain HPV genomic material but do not contain HPV viral capsid antigen at levels detectable by immunologic methods.

1. The Papillomavirus Filamentous Latent Proteins

HPV-infected cells that maintain the virus in a latent state are now known to produce a papillomavirus-specific filamentous protein (i.e., a protein found associated with filamented components of the cell) of about 54 kilodaltons (kd) in molecular weight when measured by polyacrylamide gel electrophoresis in the presence of sodium dodecyl sulfate (SDS-PAGE) as described in Example 5. For instance, the 54 kd filamentous protein is detectable in CaSki and SiHa cells as described in Example 5. CaSki and SiHa cells are cervical carcinoma-derived cell lines that contain HPV type 16 and are available from the American Type Culture Collection (ATCC; Rockville, Md.) as CRL 1550 and HTB 35, respectively.

The 54 kd filamentous protein is further characterized as possessing epitopes that are immunologically cross-reactive with the HPV polypeptides 235 and 247 as shown in Table 1. That is, the 54 kd filamentous protein contains amino acid residue sequences homologous to the sequences of polypeptides 235 and 247.

Tissue latently infected with HPV also produces a filamentous protein of 48 kd, as determined by SDS-PAGE. The 48 kd filamentous protein is detectable in CaSki cells using the immunoblotting method described in Example 5.

The 48 filamentous protein is further characterized as possessing epitopes that are immunologically cross-reactive with polypeptides 235, 247 and 245, and thus contains amino acid residue sequences homologous to those polypeptides.

2. The Papillomavirus Latent Nuclear Protein

Cells latently infected with HPV expressed a HPV specific protein of about 51 kd as measured by SDS-PAGE, that is detectable in the nucleus of Caski cells. The 51 kd nuclear protein is further characterized as possessing an epitope that is immunologically cross-reactive with polypeptide 245 derived from the amino acid residue sequence of the E2 ORF internal region.

Cells latently infected with HPV express additional nuclear proteins of 26 kd, 48 kd and 58kd as determined by SDS-PAGE.

The 26 kd, 48 kd and 58 kd proteins are detectable in HPV infected cells using the immunoblotting method described in Example 16a, and are further characterized as possessing epitopes that are immunologically cross-reactive with polypeptide 245.

3. The Papillomavirus Latent Diffuse Protein

The diffuse protein is a papillomavirus latent protein having an apparent molecular weight of about 112 kd when measured by SDS-PAGE as described in Example 5. The 112 kd diffuse protein is detectable in HeLa and SiHa cells using the immunoblotting method also described in Example 5.

HeLa cells are cervical carcinoma tissue culture cells that contain HPV type 18 and are available from the ATCC as CCL2.

The 112 kd diffuse protein is further characterized as possessing epitopes that are immunologically cross-reactive with polypeptides 236, 245, 235, 238 and 247 derived from the amino acid residue sequence of the E1 ORF internal region, the E2 ORF internal region, the Ela ORF amino terminal region, the E1 ORF internal region and the E6 ORF internal region, respectively.

The various species of latent papillomavirus proteins described hereinabove are useful in substantially pure form as proteinaceous immunogens in an inoculum of the present invention or as antigens in a diagnostic system of the present invention.

Thus, the present invention contemplates each of the above described filamentous, nuclear and diffuse papillomavirus latent proteins in substantially pure form. By "substantially pure form" is meant that the particular HPV latent protein is present in a composition that is substantially free of other papillomavirus-related proteins.

Methods for producing a characterized protein in substantially pure form are well known in the art. Typically, those methods include isolating the protein from cells containing the protein using well known biochemical techniques. For instance, the methods of gel filtration, gel chromatography, ultrafiltration, electrophoresis, ion exchange, affinity chromatography and the like, such as are known for protein fractionations, can be used to isolate the papillomavirus latent proteins found in latently infected HPV containing cultures. Because each of the latent proteins described herein are characterized in part by their immunologic cross-reactivity to defined polypeptides, immunochemical purification methods, such as immunoaffinity, immunoadsorption and the like, are particularly well adapted to producing the latent proteins in substantially pure form. Preferably, the composition is also substantially free of entities such as ionic detergents, e.g., sodium dodecyl sulfate (SDS), polyacrylamide and tissue or cell culture-derived proteins having an apparent molecular weight of less than about 40 kd as determined by SDS-PAGE.

C. Polypeptides

A polypeptide of the present invention contains no more than about 50, more usually fewer than about 35 and preferably fewer than about 25 amino acid residues, and contains at least about 5 residues. In addition, a polypeptide of the present invention is characterized by its amino acid residue sequence and novel functional properties.

Amino acid residues present in a polypeptide of the invention in addition to a sequence specifically enumerated hereinafter up to a total of no more than about 50 amino acid residues can be any residues that do not materially affect the basic and novel characteristics of a polypeptide as are discussed hereinafter. Such additional residues are usually added to one or both termini of an enumerated polypeptide and can include repeats and partial repeats of an enumerated polypeptide sequence.

Broadly, the present invention contemplates a polypeptide that includes an amino acid residue sequence capable of producing (inducing) antibody molecules that immunoreact with a papillomavirus latent protein. Preferably a polypeptide of this invention immunoreacts with antibodies induced by a latent papillomavirus infection, i.e., anti-latent papillomavirus protein antibodies. Further, the polypeptide contains an amino acid residue sequence that corresponds to a portion of the amino acid residue sequence deduced from the nucleic acid sequence of those open reading frame (ORF) regions of the papillomavirus genome known to encode latent papillomavirus proteins.

It should be understood that a polypeptide of the present invention need not be identical to the amino acid residue sequence of a latent papillomavirus protein, so long as it is able to produce, upon immunization, an antisera that contains antibody molecules that immunoreact with a latent papillomavirus protein. Preferably, the subject polypeptide is able to immunoreact with antibodies induced by a latent papillomavirus infection. Therefore, a polypeptide of the present invention can be subjected to various changes, such as insertions, deletions and substitutions, either conservative or non-conservative, where such changes provide for certain advantages in their use.

Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite antibody inducing activity.

When a polypeptide of the present invention has a sequence that is not identical to the sequence of a latent papillomavirus protein because one or more conservative or non-conservative substitutions have been made, usually no more than about 20% and more usually no more than 10% of the amino acid residues are substituted, except where additional residues have been added at either terminus for the purpose of providing a "linker" by which the polypeptides of this invention can be conveniently affixed to a label or solid matrix, or antigenic carrier. Labels, solid matrices and carriers that can be used with the polypeptides of this invention are described hereinafter.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-$NH_2$ acylation, e.g., acetylation, or thioglycolic acid amidation, terminal-carboxlyamidation, e.g., ammonia, methylamine, etc.

The peptides of the invention can contain at least one cysteine residue, and in certain instances two of such residues. Accordingly, the subject peptides can exist in various oxidative forms. In addition to the monomeric form in which the sulfhydryl group of the cysteine residue(s) is reduced, there can also exist dimeric or polymeric forms in which sulfhydryl groups on two or more peptide molecules become oxidized and form inter- and intrapeptide disulfide bonds. While subject peptides that possess only one cysteine residue can form only linear dimers, those that possess two cysteine residues can form cyclic monomers or linear or cyclic dimers and linear polymers of various lengths. These various oxidative forms are considered part of the subject invention and are included in the terms "polypeptides" and "peptides".

When coupled to a carrier via a linker to form what is known in the art as a carrier-hapten conjugate, a polypeptide of the present invention is capable of inducing antibodies that immunoreact with a latent papillomavirus protein when said protein is present in a sample that contains a latent papillomavirus infection. Representative immunoreactions between a latent papillomavirus protein and antibodies that were induced using polypeptides of the present invention are described in Example 5.

In view of the well established principle of immunologic cross-reactivity, the present invention therefore contemplates antigenically related variants of the polypeptides of the present invention. An "antigenically related variant" is a polypeptide that includes at least a six amino acid residue sequence portion of a latent papillomavirus protein and which is capable of inducing antibody molecules that immunoreact with a latent papillomavirus protein when said protein is present in a sample that contains a latent papillomavirus infection.

A polypeptide of the present invention can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Yound, "Solid Phase Peptide Synthesis", W. H. Freeman Co., San Francisco, 1969; M. Bodanszky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

Preferred polypeptides of the present invention are deduced from the nucleotide sequence of the E1, E2 or E6 ORFs of papillomaviruses, preferably HPVs.

More preferably, polypeptides of the present invention are deduced from the nucleotide sequence of specific HPVs known to cause genital papilloma virus infections, including HPV types 6, 11, 16, 18, 33, 35, 52 and the like.

1. HPV Type 16-Related Polypeptides

Figure 1:
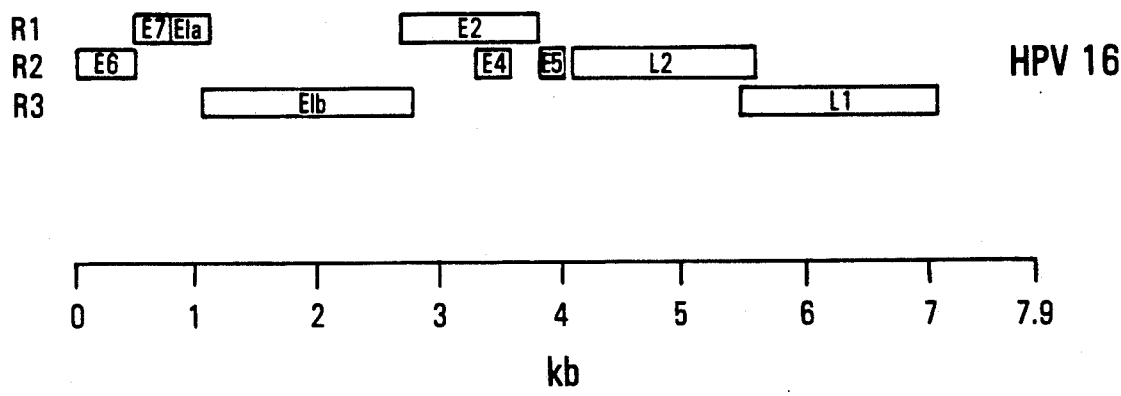
FIG. 1 shows a schematic representation of the open reading frames (ORFs) deduced from the nucleotide sequence of HPV type 16. Using the numbering system of the HPV type 16 nucleotide sequence described by Seedorf et al., *Virol*, 145:181-185 (1985), which disclosure is hereby incorporated by reference, the ORFs shown in FIG. 1 include the nucleotide sequences contained in that disclosure for each ORF as follows.

A HPV type 16-related polypeptide of the present invention contains at least 5, preferably at least 12, amino acid residues and includes a sequence that corresponds to portions of the amino acid residue sequence deduced from the E1, E2 or E6 ORFs of HPV type 16 as shown in FIG. 1. Preferably, the HPV Type-16 related polypeptides of this invention do not contain the amino acid residue sequence WRQRDQFLSQV.

Preferred polypeptides of the present invention include those whose amino acid residue sequences are shown in Table 1.

TABLE 1

Human Papillomavirus Polypeptides

| ORF[1] SEQUENCE | POLYPEPTIDE DESIGNATION | AMINO ACID RESIDUE |
|---|---|---|
| E1a | 235 | MADPAGTNGEEGTGC |
| E1 | 236 | HEDEDKENDGDSLPTC |
| E1 | 238 | RPFKSNKSTCC |
| E1 | 246 | CCDWCIAAFGLTPSI |
| E2 | 237 | TYDSEWQRDQFLSQVKIPC |
| E2 | 245 | HKSAIVTLTYDSEWQRDQC |
| E6 | 247 | CINCQKPLCPEEKQRH |

[1]The nomenclature for open reading frames (ORFs) corresponds to the ORFs shown in FIG. 1 from which the polypeptide amino acid sequence was derived.

A preferred HPV type 16-related polypeptide contains an amino acid residue sequence that corresponds to a portion of the amino acid sequence deduced from the E2 ORF of HPV type 16 and includes an amino acid residue sequence represented by the formula —TYDSE—. Preferably, the included sequence is represented by the formula —LTYDSE—.

More preferably, a HPV type 16-related polypeptide of the present invention is one defined by the amino acid residue sequence represented by the formula:

—BYDSB'—;

wherein B is at least one of the following sequence of amino acid residues:

—SAIVTLT,
SAIVTLT,
AIVTLT,
IVTLT,
VTLT,
TLT,
LT, or
T; and wherein B' is at least one of the following sequence of amino acid residues:

E—, or
E.

A more preferred HPV type 16-related polypeptide of the present invention includes an amino acid residue sequence represented by the formula —SAIVTLTDYSE— or —HKSAIVTLTDYSE—.

Still more preferred is a HPV type 16-related polypeptide defined by the amino acid residue sequence represented by the formula:

—BKSAIVTLTYDSB'—;

wherein B is at least one of the following sequence of amino acid residues:

SSTWHWTGHNVKH,
STWHWTGHNVKH,
TWHWTGHNVKH,
WHWTGHNVKH,
HWTGHNVKH,
WTGHNVKH,
TGHNVKH,
GHNVKH,
HNVKH,
NVKH,
VKH,
KH, or
H; and wherein B' is at least one of the following sequence of amino acid residues:

EWQRDQ,
EWQRD,
EWQR,
EWQ,
EW, and
E.

In a related embodiment, a HPV type 16-related polypeptide contains an amino acid residue sequence that corresponds to a portion of the amino acid sequence deduced from the E2 ORF of HPV type 16 and includes at least one of the following amino acid residue sequences —HKSAIV—,
—SAIVTL—, and
—IVTLTD—.

Preferred HPV type 16-related polypeptides contain no more than about 30 amino acid residues, have as a part of their amino acid residue sequence at least one of the following sequences:

```
        —IVTLTD—,
        —SAIVTL—,
        —HKSAIV—,
        —HKSAIVTLTDYSE—,
        —SAIVTLTDYSE—,
            —LTDYSE—, and
            —TDYSE—; and
``` are homologous, preferably without insertion or deletion, and more preferably are identical, to a portion of the HPV type 16 sequence represented by the formula:

—SSTWHWTGHNVKHKSAIVTLTYD-SEWQRDQ.

Preferred specific HPV type 16-related polypeptides include those whose amino acid residue sequences are shown in Table 2.

TABLE 2

| POLY-PEPTIDE DESIGNATION | AMINO ACID RESIDUE SEQUENCE |
|---|---|
| 66 | SSTWHWTGHNVKHKSAIVTLTYD |
| 71 | HKSAIVTLTYDSEWQRDC |
| 72 | HKSAIVTLTYDSEWQRC |
| 73 | HKSAIVTLTYDSEWQC |
| 74 | HKSAIVTLTYDSEWC |
| 75 | HKSAIVTLTYDSEC |
| 76 | HKSAIVTLTYDSC |
| 77 | HKSAIVTLTYDC |
| 78 | HKSAIVTLTYC |
| 79 | KSAIVTLTYDSEWQRDQC |
| 80 | SAIVTLTYDSEWQRDQC |
| 81 | AIVTLTYDSEWQRDQC |
| 82 | IVTLTYDSEWQRDQC |
| 83 | VTLTYDSEWQRDQC |
| 84 | TLTYDSEWQRDQC |
| 85 | LTYDSEWQRDQC |

Another preferred HPV type 16 related polypeptide of the present invention is as a polypeptide comprising no more than about 50 amino acid residues and including an amino acid residue sequence represented by the formula:

XZX', wherein Z is an amino acid residue sequence containing at least 5 amino acid residues having a sequence corresponding to a portion of the sequence represented by the formula:

HKSAIVTLTYDSE, wherein X is hydrogen or at least one amino acid residue, and wherein X' is hydroxyl or at least one amino acid residue, said polypeptide being capable of immunoreacting with anti-HPV latent protein antibodies.

Another preferred HPV type 16-related polypeptide is as a polypeptide comprising no more than about 50 amino acid residues and including an amino acid residue sequence having the formula:

XTYDSEX', wherein X is hydrogen or at least one or more amino acid residue, and wherein X' is hydroxyl or at least one amino acid residue with the proviso that X' does not include the amino acid residue sequence WQRDQFLSQV. In one embodiment, X' is an amino acid residue sequence represented by a formula selected from the group consisting of:

```
        W,
        WQ,
        WQR,
        WQRD, and
        WQRDQ.
```

In a preferred embodiment, X' is an amino acid residue sequence represented by a formula selected from the group consisting of:

```
        WQRDQF, and
        WQRDQFL.
```

In another preferred embodiment X' is an amino acid residue sequence represented by a formula selected from the group consisting of:

```
        WQRDQFLS, and
        WQRDQFLSQ.
```

Still another way of defining a preferred HPV type 16-related polypeptide is as a polypeptide comprising no more than about 50 amino acid residues and including at least one of the following amino acid residue sequences:

```
        —TDYSE—,
        —LTDYSE—,
        —SAIVTLTDYSE—,
        —HKSAIVTLTDYSE—,
        —HKSAIV—,
        —SAIVTL—, and
        —IVTLTD—; and
``` wherein said polypeptide does not contain the amino acid residue sequence WRQRDQFLSQV.

2. HPV Type 6-Related Polypeptides

A HPV type 6-related polypeptide of the present invention contains an amino acid residue sequence that corresponds to a portion of the amino acid residue sequence deduced from the E2 ORF of HPV type 6 and includes an amino acid residue sequence represented by the formula —HAIVTVTYDSE—.

A preferred HPV type 6-related polypeptide has an amino acid residue sequence represented by the formula HKHAIVTVTYDSEEQRQQC.

3. HPV Type 11-Related Polypeptides

A HPV type 11-related polypeptide of the present invention contains an amino acid residue sequence that corresponds to a portion of the amino acid residue sequence deduced from the E2 ORF of HPV type 11 and includes an amino acid residue sequence represented by the formula —NAIVTLTYSSE—.

A preferred HPV type 11-related polypeptide has a amino acid residue sequence represented by the formula HKNAIVTLTYSSEEQRQQC.

4. HPV Type 18-Related Polypeptides

A HPV type 18-related polypeptide of the present invention contains an amino acid residue sequence that corresponds to a portion of the amino acid residue sequence deduced from the E2 ORF of HPV type 18 and includes an amino acid residue sequence represented by the formula —ILTVT—, and more preferably includes a sequence represented by the formula —TGTLT-VTYHSE—.

A preferred HPV type 18-related polypeptide has an amino acid residue sequence represented by a formula selected from the group consisting of:

EKTGILTVTYHSETQRTKC, and
NEKTGILTVTYHSETQRTKC.

5. HPV Type 33-Related Polypeptides

A HPV type 33-related polypeptide of the present invention contains an amino acid residue sequence that corresponds to a portion of the amino acid residue sequence deduced from the E2 ORF of HPV type 33 and includes an amino acid residue sequence represented by the formula —NGIVTVTFVTE—.

A preferred HPV type 33-related polypeptide has an amino acid residue sequence represented by the formula SKNGIVTVTFVTEQQQQMC.

Preferred HPV related polypeptides deduced from the E2 ORF of HPV types 6, 11, 18 and 33 are shown in Table 3.

TABLE 3

| Polypeptide Designation | HPV Type | Amino Acid Residue Sequence |
|---|---|---|
| K70 | 6 | HKHAIVTVTYOSEEQRQQC |
| K71 | 11 | HKNAIVTLTYSSEEQRQQC |
| K69 | 18 | EKTGILTVTYHSETQRTRC |
| K68 | 18 | NEKTGILTVTYHSETQRTRC |
| K72 | 33 | SKNGIVTVTFVTEQQQQMC |

The present invention also contemplates a composition containing a polypeptide of the present invention admixed in a physiologically tolerable diluent. Such compositions typically contain the polypeptide at a concentration in the range of micromolar to molar, preferably millimolar.

In addition, the present invention contemplates fusion proteins, and composition thereof, comprising a polypeptide of the present invention operatively linked (fused) to at least one amino acid residue sequence, wherein said sequence is heterologous to a sequence deduced from a papillomavirus latent protein ORF.

D. Inocula

In another embodiment, a polypeptide of this invention, an antigenically related variant thereof or a substantially pure papillomavirus latent protein of this invention is used in a pharmaceutically acceptable aqueous diluent composition to form an inoculum that, when administered in an effective amount, is capable of inducing antibodies that immunoreact with papillomavirus latent protein.

The word "inoculum" in its various grammatical forms is used herein to describe a composition containing a polypeptide or a substantially pure papillomavirus latent protein of this invention as an active ingredient used for the preparation of antibodies against a papillomavirus latent protein.

When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide", and its various grammatical forms.

For a polypeptide that contains fewer than about 35 amino acid residues, it is preferable to use the peptide bound to a carrier for the purpose of inducing the production of antibodies as already noted.

As previously noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318–326 (1983) and the like, or the use of carbodiimide technology as in the use of a water-soluble carbodiimide to form amide links to the carrier. For a review of protein conjugation or coupling through activated functional groups, see Aurameas, et al., *Scand. J. Immunol.*, Vol. 8, Supp-1. 7, 7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide or latent papillomavirus protein of this invention, and for a polypeptide it is typically as a conjugate linked to a carrier. The effective amount of polypeptide or protein per unit dose depends, among other things, on the species of animal inoculated, the body weight of the animal and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to' be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable)

diluent or vehicle such as water, saline or phosphate-buffered saline to form an aqueous composition. Similarly, inocula containing latent papillomavirus protein are typically prepared from substantially pure latent papillomavirus protein by dispersion in the same physiologically tolerable diluents. Such diluents are well known in the art and are discussed, for example, in *Remington's Pharmaceutical Sciences*, 16th Ed., Mack Publishing Company, Easton, Pa. (1980) at pages 1465–1467.

Inocula can also include an adjuvant as part of the diluent. Adjuvants such as complete Freund's adjuvant (CFA), incomplete Freund's adjuvant (IFA) and alum are materials well known in the art, and are available commercially from several sources.

E. Antibodies and Anti-Polypeptide Antibodies

The term "antibody" in its various grammatical forms is used herein to refer to a composition containing a population of immunoglobulin molecules and/or immunologically active portions of immunoglobulin molecules, i.e., molecules that contain an antibody combining site or paratope.

An "antibody combining site" is that structural portion of an antibody molecule comprised of a heavy and light chain variable and hypervariable regions that specifically binds (immunoreacts with) antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies my methods that are well known. See for example, U.S. Pat. No. 4,342,566 to Theofilopolous and Dixon. Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

The term "immunoreact" in its various forms means binding between an antigenic determinant-containing molecule and a molecule containing an antibody combining site such as a whole antibody molecule or a portion thereof.

An immunoreaction forms an immunoreaction product that contains an antibody combining site and the bound antigenic determinant. An immunoreaction is substantial if the binding results in the production of an amount of immunoreaction product that is measurable by methods such as ELISA, immunoblotting, immunostaining or the like as described herein.

"Antigenic determinant" refers to the actual structural portion of the antigen that is immunologically bound by an antibody combining site. The terms is also used interchangeably with "epitope".

An antibody of the present invention is characterized as containing substantially isolated or substantially pure antibody molecules that immunoreact with one of the following papillomavirus latent proteins:

a) the 112 kd diffuse protein;
b) the 54 kd filamentous protein,
c) the 48 kd filamentous protein,
d) the 51 kd nuclear protein,
e) the 58 kd nuclear protein,
f) the 26 kd nuclear protein, or
g) the 48 kd nuclear protein.

By "substantially isolated" is meant that at least about 10%, preferably at least about 25%, and more preferably at least about 50%, of the antibody molecules present in the antibody are directed against a papillomavirus latent protein or papillomavirus related polypeptide.

By "substantially pure" is meant that at least 1%, preferably at least 10%, and more preferably at least 50%, of the protein present in the antibody is protein molecules that form antibody combining sites. In preferred embodiments, a contemplated antibody does not immunoreact with:

a) a 70 kd protein present in HeLa cells,
b) a 20 kd protein present in CaSki cells,
c) a 15 kd protein present in CaSki cells,
d) a 11 kd protein present in CaSki cells, or
e) a 10 kd protein present in CaSki cells.

In another embodiment, the present invention contemplates an anti-polypeptide antibody containing antibody molecules that immunoreact with (1) a polypeptide, and preferably only one polypeptide, of the present invention, and (2) at least one of the papillomavirus latent proteins selected from the group consisting of:

a) the 112 kd diffuse protein;
b) the 54 kd filamentous protein;
c) the 48 kd filamentous protein;
d) the 51 kd nuclear protein; and
e) the 58 kd nuclear protein.

In preferred embodiments, a contemplated anti-polypeptide antibody does not substantially immunoreact with:

a) a 70 kd protein present in HeLa cells,
b) a 20 kd protein present in CaSki cells,
c) a 15 kd protein present in CaSki cells,
d) a 11 kd protein present in CaSki cells, or
e) a 10 kd protein present in CaSki cells;

More preferred is a polyclonal anti-polypeptide antibody wherein the antibody molecules immunoreact with a polypeptide, preferably only one of the polypeptides, selected from the group consisting of:

MADPAGTNGEEGTGC,
HEDEDKENDGDSLPTC,
RPFKSNKSTCC,
CCDWCIAAFGLTPSI,
TYDSEWQRDQFLSQVKIPC,
HKSAIVTLTYDSEWQRDQC, and
CINCQKPLCPEEKQRH.

Still further preferred are anti-polypeptide antibodies prepared by immunizing a non-human mammal, such as a goat, horse, rabbit and the like. Exemplary anti-polypeptide antibodies are those prepared in rabbits, designated herein as anti-235, anti-236, anti-237, anti-238, anti-245, anti-246 and anti-247.

An antibody of the present invention is typically produced by immunizing a mammal with an inoculum of the present invention and thereby induce in the mammal antibody molecules having the appropriate polypeptide immunospecificity. The antibody molecules are then collected from the mammal and isolated or purified to the extent desired by well known techniques such as, for example, by immunoaffinity chromatography. The isolated antibody molecule-containing compositions are then evaluated for their ability to immunoreact according to the described immunospecificity, and those compositions so prepared having the appropriate immunospecificity are retained as antibody compositions of the present invention. The antibody so produced can be used in, inter alia, the diagnostic methods and systems of the present invention to assay for the presence of latent papillomavirus proteins in a body sample.

The antibodies of this invention induced by a polypeptide of this invention, can be described as being oligoclonal as compared to naturally occurring polyclonal antibodies since they are raised to an immunogen (the relatively small polypeptide) having relatively few epitopes as compared to the epitopes mimicked by an intact viral latency-associated papillomavirus-encoded protein. Consequently, antibody molecules of this invention bind to epitopes of the polypeptide, whereas naturally occurring antibodies raised to whole latent papillomavirus protein molecules bind to epitopes throughout those protein molecules and are referred to as being polyclonal.

In another embodiment, an antibody of the present invention is characterized as containing substantially isolated antibody molecules that immunoreact with a latent papillomavirus protein related polypeptide, i.e., a polypeptide deduced from a latent protein ORF, preferably E1, E2 or E6. Preferred are substantially isolated antibody molecules that immunoreact with a polypeptide having the formula:

---
SSTWHWTGHNVKHKSAIVTLTYDSEWQRDC,
EKTGILTVTYHSETQRTRC,
HKHAIVTVTYOSEEQRQQC,
HKNAIVTLTYSSEEQRQQC, or
SKNGIVTVTFVTEQQQQMC.
---

These antibodies are typically produced by immunoaffinity chromatography, using immobilized latent papillomavirus protein-related polypeptides, from anti-latent papillomavirus protein antibody-containing sera, such as is found in a patient having a latent papillomavirus infection. Preferred antibodies of this embodiment are human antibodies, isolated from the sera of a patients having a latent papillomavirus infection, preferably an infection caused by a type 16, 18, 6, 11 or 33 human papillomavirus, or the like. Particularly preferred are the human antibodies prepared in Example 15.

F. *Monoclonal Antibody Compositions*

A monoclonal antibody contains antibody molecules that immunoreact with papillomavirus latent protein is also contemplated. The phrase "monoclonal antibody" in its various grammatical forms refers to a population of antibody molecules that contains only one species of antibody combining site capable of immunoreacting with a particular antigen. A monoclonal antibody composition thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

A monoclonal antibody composition is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, *Nature*, 256:495–497 (1975), which description is incorporated by reference.

In one embodiment, monoclonal antibody composition of the present invention is characterized as containing antibody molecules that immunoreact with one of the following papillomavirus latent proteins:

a) the 112 kd diffuse protein,
b) the 54 kd filamentous protein,
c) the 48 kd filamentous protein,
d) the 51 kd nuclear protein,
e) the 58 nuclear protein,
f) the 26 kd nuclear protein, or
g) the 48 kd nuclear protein.

Preferably, a monoclonal antibody of this invention does not substantially immunoreact with:

a) a 70 kd protein present in HeLa cells,
b) a 20 kd protein present in CaSki cells,
c) a 15 kd protein present in CaSki cells,
d) a 11 kd protein present in CaSki cells, or
e) a 10 kd protein present in CaSki cells.

In another embodiment, the present invention contemplates an anti-polypeptide monoclonal antibody containing antibody molecules that immunoreact with a polypeptide of the present invention and a papillomavirus latent protein. Preferably, an anti-polypeptide monoclonal antibody does not substantially immunoreact with:

a) a 70 kd protein present in HeLa cells,
b) a 2 kd protein present in CaSki cells,
c) a 15 kd protein present in CaSki cells,
d) a 11 kd protein present in CaSki cells, or
e) a 10 kd protein present in CaSki cells.

In preferred embodiments, a monoclonal antibody immunoreacts with a polypeptide whose amino acid residue sequence corresponds to a polypeptide shown in Table 1, 2 or 3. A particularly preferred monoclonal antibody contains antibody molecules capable of being produced by a hybridoma shown in Table 4.

TABLE 4

| Monoclonal Antibody Producing Hybridomas | | |
| --- | --- | --- |
| ORF[1] | POLYPEPTIDE[2] DESIGNATION | HYBRIDOMA DESIGNATION |
| E1 | 235 | 235:B9 |
| E1 | 238 | 238:8E9 |
| E2 | 245 | 245:11E3 |
| E6 | 247 | 247:4D11 |
| E6 | 247 | 247:10F7 |
| E6 | 247 | 247:11D11 |

[1]The nomenclature for open reading frames (ORFs) corresponds to the ORFs shown in FIG. 1 from which the polypeptide amino acid sequence was derived.
[2]Polypeptides have amino acid sequences as shown in Table 1.

Preferred monoclonal antibody producing hybridomas designated 235:B9, 245:11E3 and 247:4D11 were deposited as hybridoma cultures with the American Type Culture Collection (ATCC), Rockville, Md., on May 12, 1988 and were assigned accession numbers. HB 9720, HB 9718 and HB 9719, respectively.

In another embodiment, the present invention contemplates an anti-polypeptide monoclonal antibody containing antibody molecules that immunoreact with a polypeptide having the formula:

---
SSTWHWTGHNVKHKSAIVTLTYDSEWQRDC,

-continued

EKTGILTVTYHSETQRTRC,
HKHAIVTVTYOSEEQRQQC,
HKNAIVTLTYSSEEQRQQC, or
SKNGIVTVTFVTEQQQQMC.

A monoclonal antibody of the present invention can be produced by initiating a monoclonal hybridoma culture comprising a nutrient medium containing a hybridoma of the present invention that secretes antibody molecules of the appropriate immuno specificity. The culture is maintained under conditions and for a time period sufficient for the hybridoma to secrete the antibody molecules into the medium. The antibody-containing medium is then collected. The antibody molecules can then be further isolated by well known techniques.

To produce a much greater concentration of slightly less pure monoclonal antibody, the desired hybridoma may be injected into mice, preferably syngenic or semi-syngenic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse.

Media useful for the preparation of these compositions are both well known in the art and commercially available and include synthetic culture media, inbred mice and the like. An exemplary synthetic medium is Dulbecco's minimal essential medium [DMEM; Dulbecco et al., *Virol.* 8:396 (1959)] supplemented with 4.5 gm/l glucose, 20 mm glutamine, and 20% fetal calf serum. An exemplary inbred mouse strain is the Balb/c.

The monoclonal antibody compositions produced by the above method can be used, for example, in diagnostic and immunopurification modalities wherein formation of a papillomavirus latent protein-containing immunoreaction product is desired.

G. Hybridomas and Other Monoclonal Antibody Producing Cells, and Methods of Preparation Hybridomas of the present invention are those which are characterized as having the capacity to produce a monoclonal antibody of the present invention.

Methods for producing hybridomas producing (secreting) antibody molecules having a desired immunospecificity, i.e., having the ability to immunoreact with a particular protein, an identifiable epitope on a particular protein and/or a polypeptide, are well known in the art. Particularly applicable is the hybridoma technology described by Niman et al., *Proc. Natl. Acad. Sci. USA.* 80:4949-4953 (1983), and by Galfre et al., *Meth. Enzymol.*, 73:3-46 (1981), which descriptions are incorporated herein by reference.

Typically, hybridomas of the present invention are produced by using, in the above techniques as an immunogen, a substantially pure latent papillomavirus protein or a polypeptide of the present invention.

H. Diagnostic Systems

A diagnostic system in kit form of the present invention includes, in an amount sufficient for at least one assay, a substantially pure papillomavirus latent protein, polypeptide, antibody, anti-polypeptide antibody, monoclonal antibody or anti-polypeptide monoclonal antibody of the present invention, as a separately packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for the presence of a latent papillomavirus infection in a body sample comprises a package containing an antibody of the present invention that immunoreacts with a latent papillomavirus protein. Preferably, the antibody is a monoclonal antibody of the present invention. More preferably, the antibody molecules are those of the antibody produced by a hybridoma of the present invention. Further preferred are kits wherein the antibody molecules are linked to an enzyme label.

Thus, in preferred embodiments, a diagnostic system of the present invention further includes a label or indicating means capable of signaling the formation of a complex containing an antibody molecule or polypeptide of the present invention.

The word "complex" as used herein refers to the product of a specific binding reaction such as an antibody-antigen reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in a substantially pure latent papillomavirus protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel protein methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), alkaline phosphatase, glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine or orthophenylenediamine. An additional reagent useful with glucose oxidase is 2,2'-azino-di-(3-ethyl-benz-thiazoline-G-sulfonic acid) (ABTS).

Radioactive elements are also useful labeling agents. An exemplary radiolabeling agent is a radioactive element that produces gamma ray emissions. Elements which themselves emit gamma rays, such as $^{124}I$, $^{125}I$ $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}$indium or $^{3}H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a substantially pure protein, polypeptide, or antibody molecule of the present invention. Exemplary specific binding agents are second antibody molecules, complement proteins or fragments thereof, *S. aureus* protein A and the like. Preferably, the specific binding agent can bind the antibody molecule or polypeptide of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of antibody molecule that immunoreact with a latent papillomavirus protein present in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in preferred embodiments, the substantially pure protein, polypeptide, or antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; latex; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

In another embodiment a diagnostic system of the present invention is useful for assaying for the presence of antibodies induced by a latent papillomavirus infection, i.e., anti-latent papillomavirus protein antibodies. Such a system comprises, in kit form, a package containing a latent papillomavirus protein or a polypeptide of this invention. Preferably the included polypeptide contains a sequence homologous to a portion of a deduced amino acid residue sequence derived from the E region open reading frames (ORFs) of a sequenced papillomavirus genome. More preferably, the included polypeptide contains a sequence deduced from the E1, E2 or E6 ORF of a HPV.

In one embodiment, it is preferred to include in a contemplated diagnostic system a polypeptide that is related to a particular HPV type, such as is disclosed herein for types 6, 11, 16, 18, 33, and 35. It is particularly preferred to include a HPV type 6, 11, 16, 18, or 13 related polypeptide of the present invention, preferably one of those whose sequence is shown before in Tables 1, 2 or 3.

In view of the results discussed in the Examples, it is clear that a significant antigenic determinant of the human papillomavirus which reacts with HPV type 16 latent protein-induced antibodies is defined by (contained within) the five amino acid residue sequence —TYDSE— described before. Moreover, even though each of the HPV type 16 related polypeptides of the present invention reacts with most anti-HPV type 16 latent protein antibody containing sera, individual patient sera have been observed to react specifically with one of the HPV type 16 related polypeptides but not another. This observation indicates that additional antigenic determinants exist in other peptides containing a sequence that includes the formula —LTYDSE—, —SAIVTLTDYSE—, —HKSAIVTLTDYSE—, —HKSAIV—, —SAIVTL—, or —IVTLTD—, as described before.

Therefore, the present invention further contemplates the discovery that recognition of antibodies to HPV type 16 latent proteins in immunological assays is significantly enhanced if the above described HPV type 16-related polypeptides are used in combination with a different species of HPV type 16-related polypeptide. An exemplary and preferred embodiment includes in combination polypeptides 66 and 245, or 78 and 85, or 66 and 78 and 85, and the like combinations.

Thus in one embodiment a diagnostic system contains more than one species of HPV type 16 related polypeptide of the present invention. Preferably the polypeptide species are present in the system as an admixture, although individual species may be present in separate packages or segregated into separate locations in the system. This combination format provides the ability to detect in a single kit, or preferably on a single solid support if admixed, anti-HPV latent protein antibodies having different immunospecificities, thereby improving the screening capabilities of such a system.

When it is desired to provide a diagnostic system capable of being used to detect and distinguish between exposure to different papillomavirus types, the kit contains more than one polypeptide wherein the additional polypeptides are selected on the basis of their ability to produce antibody molecules, upon immunization, that immunoreact with the latent papillomavirus proteins from a second virus type that is different from the virus type from which the first polypeptide was derived. Furthermore, the additional polypeptides induce antibody molecules that do not immunoreact with the latent papillomavirus proteins expressed by the first virus type. Thus, as used herein, "different" means that there is a substantial measurable difference in the ability of the two polypeptide-induced antibody molecule compositions to immunoreact with latent papillomavirus proteins produced in a latent infection by a single papillomavirus type. Thus, it is said that the polypeptides are type-specific in their ability to induce antibody compositions that do not both immunoreact with the latent papillomavirus proteins of a single virus type.

Stated alternatively, polypeptides are "different" and therefore type-specific where there is a substantial measurable difference in their ability to immunoreact with antibodies induced by a papillomavirus latent protein of one type when compared to their ability to immunoreact with the protein of another type. A difference in immunoreaction when measured by ELISA, as in Example 14, is substantial if there is more than a 0.05, more preferably a 0.1 and still more preferably a 0.4 difference in optical density.

Preferred type specific polypeptides for inclusion in this embodiment of the present diagnostic system include the HPV type 16 related, type 18 related, type 6 related, type II related, and type 33 related polypeptides described before. Exemplary uses of type specific polypeptide of the present invention in a diagnostic system are shown in Example 14.

In this embodiment of a diagnostic kit utilizing type specific polypeptides it is contemplated that the polypeptides may be provided physically separated within the kit thereby allowing for distinguishing between the presence of antibodies that immunoreact with one or the other of the included polypeptides. An exemplary kit of this type includes a first solid support having operatively affixed thereto a first polypeptide and a second solid support having operatively affixed thereto a second polypeptide, in which the two separated polypeptides are type-specific for different papillomavirus types. Of course, the two solid supports can be on the same or different bulk medium, as in the case where the solid supports are microtiter wells, and the wells are on the same or different microtiter plates. In addition, this embodiment can include a third solid support having affixed thereto a third type-specific polypeptide whose specificity is different from both the first and second, and so on.

In another embodiment, different type-specific polypeptides may be included in a diagnostic kit as an admixture of all the peptides desired to be included, thereby creating the ability to screen for the presence of antibodies induced by latent papillomavirus infections caused by more than one papillomavirus type using one solid support. A kit of this type typically comprises a solid support such as a microtiter plate having operatively affixed thereto in an individual well an admixture of the polypeptides being type-specific for more than one papillomavirus type.

I. Assay Methods

The present invention contemplates any method that results in detecting latent papillomavirus proteins, particularly those proteins as are found in a tissue sample such as a biopsy, urethral smear or pap smear, by producing an immunocomplex containing a substantially pure latent papillomavirus protein, a polypeptide or antibody molecule contained in an antibody or monoclonal antibody composition of the present invention.

In addition, the present invention contemplates any method that results in detecting antibody molecules that immunoreact with latent papillomavirus proteins or polypeptides deduced from the nucleotide sequence of a papillomavirus genome, particularly those antibody molecules in a vascular body fluid such as are found in serum or vaginal secretions from a patient or other animal species carrying a latent papillomavirus infection, by producing an immunocomplex containing a substantially pure latent papillomavirus protein, a polypeptide or antibody molecule contained in an antibody or monoclonal antibody composition of the present invention.

Those skilled in the art will understand that there are numerous well known clinical diagnostic chemistry procedures that can be utilized to form these complexes. Thus, while exemplary assay methods are described herein, the invention is not so limited.

1. Immunohistochemical Labeling of Tissue Samples

A method for detecting the presence of a latent papillomavirus infection in tissue samples is contemplated. In this embodiment, antibody molecules of the present invention are used to detect latent papillomavirus infection by means of their ability to immunoreact with the latent papillomavirus proteins present in papillomavirus infected tissue samples such as cervical epithelial biopsy, condyloma biopsy, urethral smears and pap smears. In preferred embodiments, the antibody molecules are present as a monoclonal antibody composition and more preferably are produced by a hybridoma listed in Table 4.

For example, a biopsy sample is obtained and prepared by fixation for immunohistochemical analysis by well known techniques. See, for example, Tubbs, *Atlas of Immunohistology*, American Society of Clinical Pathology Press, Chicago. The prepared biopsy sample is admixed with an antibody molecule-containing composition of the present invention to form an immunoreaction admixture. The admixture thus formed is maintained under biological assay conditions for a time period sufficient for any latent papillomavirus proteins present in the sample to immunoreact with the added antibody molecules to form an immunoreaction product. The presence of an immunoreaction product is then assayed.

In this embodiment, antibody molecules utilized for detecting a latent papillomavirus infection in tissue samples can include substantially isolated antibody molecules that immunoreact with a latent papillomavirus protein related polypeptide, preferably a polypeptide deduced from the E2 ORF. Exemplary antibody molecules of this class are those isolated by affinity chromatography, using immobilized polypeptides having papillomavirus related sequences, and isolated from anti-latent papillomavirus protein antibody containing sera, such as is found in a patient having a latent papillomavirus infection. Exemplary are the detection methods described in Example 16 using antibody molecules affinity isolated from a HPV infected patient antisera.

2. Detection of Antibodies to Latent Papillomavirus Infection

Various heterogeneous and homogeneous assay protocols can be employed, either competitive or non-competitive, for detecting the presence and preferably amount of antibodies that immunoreact with latent papillomavirus proteins in a vascular body fluid, i.e., anti-latent papillomavirus protein antibodies.

In particular this invention contemplates an "ELISA" format as discussed herein to detect the presence and quantity of antibody molecules in a body fluid sample such as serum, plasma, vaginal secretions or urine, said antibody molecules being those that immunoreact with a latent papillomavirus protein. In this format, the method employs an antigen or antibody bound to a solid phase (solid support) and an enzyme-antigen or enzyme-antibody conjugate to detect and quantify the amount of an antibody present in the sample. In preferred embodiments the antigen bound to the solid phase is a polypeptide of the present invention.

For example, a human blood sample and a solid support containing a polypeptide of the present invention attached thereto are admixed. The admixture thus formed is maintained under biological assay conditions for a time period sufficient for any antibodies to immunoreact with the solid phase polypeptide and form an immunoreaction product. A second labeled antibody, such as horseradish peroxidase labeled anti-human IgA antibodies, is then admixed with the first immunoreaction product containing-solid support and maintained under biological assay conditions for a time period sufficient for any first immunoreaction product to immunoreact with the labeled antibodies and form a labeled second immunoreaction product. The labeled second immunoreaction products are then separated from the non-reacted labeled-antibodies, typically by washing the solid support sufficient to remove the unbound label. The amount of labeled immunoreaction product is then assayed.

Biological assay conditions are those that maintain the biological activity of the antibody molecules and polypeptide molecules of this invention and the antibody molecules sought to be assayed. Those conditions include a temperature range of about 4 degrees C. to about 45 degrees C., preferably about 37 degrees C., a pH value range of about 5 to about 9, preferably about 7 and an ionic strength varying from that of distilled water to that of about one molar sodium chloride, preferably about that of physiological saline. Methods for optimizing such conditions are well known in the art.

In preferred embodiments, the present ELISA formatted assay method utilizes polypeptides deduced from the E1, E2 or E6 ORFs of HPV type 16, particularly the polypeptides whose amino acid residue sequences are those listed in Table 1. Still more preferred are the HPV type 16 polypeptides 237, 245 and 246. Additional HPV type 16-related polypeptides preferred for use in detecting anti-latent papillomavirus proteins antibodies are those listed in Table 2.

In another embodiment, the present assay contemplates the detection of anti-HPV latent protein antibodies of human papillomaviruses of types other than type 16 by the use of HPV-related polypeptides deduced from the E2 ORF region of other genital papillomaviruses. Preferred are the HPV-related polypeptides deduced from type 6, 11, 18 and 33, particularly those shown in Table 3.

Exemplary ELISA methods utilizing various polypeptides are shown in the Examples.

3. Detection of Antibodies to Latent Papillomavirus Protein by Competition ELISA The present invention contemplates a competition assay method for detecting the presence and preferably amount of anti-latent papillomavirus protein antibodies that uses a basic ELISA in two different competition formats.

In one format, a method is contemplated for assaying a body fluid sample for the presence of anti-latent papillomavirus protein antibodies comprising the steps of:

(a) substantially simultaneously admixing a body fluid sample with (1) a polypeptide of the present invention that is affixed to a solid support and (2) a predetermined amount of a liquid-phase labeled anti-polypeptide antibody of the present invention that immunoreactes with the affixed polypeptide to form a competition immunoreaction admixture having a solid and a liquid phase. Preferably the body fluid sample is a known amount of blood, serum, plasma, urine, saliva, semen or vaginal secretion.

(b) Maintaining the admixture under biological assay conditions for a predetermined time period such as about 10 minutes to about 16 to 20 hours at a temperature of about 4 degrees C. to about 45 degrees C. that is sufficient for any anti-latent papillomavirus protein antibodies present in the sample to immunoreact with the polypeptide, and also sufficient for the labeled anti-polypeptide antibody to compete for immunoreaction with the same polypeptides to form solid phase labeled anti-polypeptide-containing immunoreaction product.

(c) Assaying for the presence of any labeled anti-polypeptide-containing immunoreaction product in the solid phase and thereby the presence of any anti-latent papillomavirus protein antibodies in the immunoreaction admixture is also determined. Preferably, the amount of any labeled anti-polypeptide-containing immunoreaction product formed is determined, and thereby the amount of anti-latent papillomavirus protein antibodies present in the sample.

In another format, a competitive ELISA of this invention comprises the steps of:

(a) substantially simultaneously admixing a body fluid sample, as in the previous format, with (1) a polypeptide of the present invention that is affixed to a solid support, and (2) a predetermined amount of the same, or an immunologically cross-reactive polypeptide in liquid phase to form a competition immunoreaction admixture having a solid and a liquid phase;

(b) maintaining the admixture under biological assay conditions for a time period sufficient for any anti-latent papillomavirus protein antibodies present in the sample to immunoreact with either the solid phase or liquid phase polypeptide to form both a solid phase and a liquid phase polypeptide-containing immunoraction product; and (c) assaying for the presence of any solid-phase polypeptide-containing immunoreaction product that formed, and thereby the presence of any anti-latent papillomavirus protein antibodies in the immunoreaction admixture is also determined.

In a different embodiment of the second format, the polypeptide in the liquid phase is not the same nor substantially immunologically cross reacting with the polypeptides in the solid phase. Thus, the two polypeptide included in the assay are different papillomavirus type-specific polypeptides in so far as "different" has been defined herein. For example, a HPV type 16-related polypeptide is present in the solid phase and a HPV 6-related polypeptide is present in the liquid phase, such as polypeptides 245 and K-70 respectively. Such a competition assay format provides for a method to distinguish the HPV type present that has induced the detected anti-HPV latent protein antibodies.

EXAMPLES

The following examples are intended to illustrate, but not limit, the present invention.

1. Polypeptide Synthesis

Polypeptides corresponding in amino acid residue sequence to portions of latent proteins encoded by various HPV type 16 E ORFs were chemically synthesized according to the solid-phase methods disclosed in U.S. Pat. No. 4,631,211, which disclosure is hereby incorporated by reference.

The amino acid residue sequence of the polypeptides synthesized and their location within the deduced amino acid sequence of HPV E region ORFs are listed in Table 1.

Additional HPV-related polypeptides were chemically synthesized by above solid-phase methods, each polypeptide having as an amino acid residue sequence one of the sequences listed in Tables 2 and 3.

2. Preparation of Polyclonal Anti-Polypeptide Antiserum a. Preparation of Reduced Polypeptide Polypeptides prepared as described in Example 1 were analyzed to determine their cysteine content. A one milliliter (ml) volume solution of PE buffer [0.1M sodium phosphate buffer, pH 7.2, 5 mM ethylenediaminetetraacetic acid (EDTA)] containing 125 micrograms (ug) of polypeptide was admixed with 100 microliters (ul) of DTNB solution (1 mM dithio nitrobenzoic acid in methanol) and maintained at room temperature for 30 minutes. The optical density (O.D.) of the resulting maintained admixture was measured at 412 nanometers (nm) against a control solution of PE buffer alone. By comparison to a standard curve using glutathione, in which a 28 ug/ml solution in PE buffer exhibits about 1.14 O.D. units at 412 nm, the amount of free cysteine was determined for each polypeptide measured. Polypeptides having less than 75 percent of the available cysteine residues oxidized were considered reduced polypeptides. Those polypeptides having more than 75 percent of the available cysteine residues oxidized were subjected to reduction as described below.

Polypeptides were reduced by admixing 10 milligrams (mg) of polypeptide with 10 mg dithiothreitol (DTT; Sigma Chemical Co., St. Louis, Mo.) in 1 ml of 50 mM phosphate buffer (pH 8.0) and maintaining the admixture at room temperature with continuous stirring agitation. After 60 minutes of agitation, 50 ul concentrated acetic acid was further admixed and the resulting admixture was then applied to a 15 ml bed volume Sephadex G-10 (Pharmacia, Piscataway, N.J.) column prewashed with 5 percent (%) acetic acid in water. The column was rinsed with 5% acetic acid and the resulting column eluant was collected in fractions. The optical density (O.D.) at 206 nm was determined for each fraction, the O.D. 206-defined fractions of the first protein peak were pooled and the pooled fractions were lyophilized to yield dried reduced polypeptide. The dried polypeptide was dissolved in acetate buffer (pH 4.0) at 5 mg/ml to yield reduced polypeptide.

b. Preparation of Polypeptide-KLH Conjugated Immunogen

Reduced polypeptide, prepared in Example 1, was conjugated to keyhole limphet hemocyanin protein (KLH; Pacific Bio-Marine Laboratories, Venice, Calif.) using the coupling reagent m-maleimidobenzoyl N-hydroxysuccinimide ester (MBS; Sigma). Two hundred ul of KLH solution, dialyzed against PB (10 mM phosphate buffer, pH 7.2) at 20 mg KLH/ml PB, was admixed with 55 ul PB and then 85 ul of MBS solution (6 mg/ml in dimethyl formamide) was admixed slowly by dropwise addition while stirring the admixture at room temperature. The resulting admixture was maintained for 30 minutes with stirring at room temperature and was then applied to a Sephadex G-25 column (Pharmacia) with a 15 ml bed volume that was previously rinsed with PB50 (50 mM phosphate buffer, pH 6.0). The column was rinsed with PB50 and the resulting column eluant was collected dropwise in fractions (35 drops per fraction). The O.D. 260 was determined for each fraction and the peak fractions were pooled. The pool was admixed with 1 ml of reduced polypeptide [5 mg/ml in acetate buffer (pH 4.0)], the resulting admixture was monitored for pH and adjusted as needed with sodium hydroxide or hydrochloric acid to maintain the admixture between pH 7.0 and 7.5, while stirring at room temperature for 3 hours. The maintained and stirred admixture was then combined with sufficient PBS (phosphate buffered saline) to make a 2.0 ml final volume to produce KLH-conjugated polypeptide solution.

c. Immunization of Rabbits to Produce Polyclonal Anti-Polypeptide Antisera

New Zealand white rabbits obtained from the SCRF Vivarium (Research Institute of Scripps Clinic, La Jolla, Calif.) were immunized using KLH-conjugated polypeptide solutions prepared in Example 2b by the following schedule of inoculations. The first inoculation comprised four subcutaneous injections administered at locations along the back, each injection having approximately 375 ul of a solution prepared by admixing 3 mg mycobacterium (DIFCO Laboratories, Detroit, Mich.), 1.5 ml incomplete Freund's adjuvant (IFA; Sigma) and 1.5 ml PBS containing 250 ul KLH-conjugated polypeptide solution, said admixture having been emulsified for five minutes prior to inoculation. The second inoculation was similarly administered 14 days after the first inoculation, using the same admixture but omitting the mycobacterium. The third inoculation was administered 21 days after the first inoculation, comprising 1 ml of a well shaken admixture of 250 ul KLH-conjugated polypeptide solution, 950 ul PBS and 800 ul aluminum hydroxide solution (10 mg/ml sterile water), injected intraperitoneally.

Antisera was obtained from the above-immunized rabbits by bleeding the ear veins 28 and 35 days after the first injection to yield rabbit anti-polypeptide antisera.

Rabbit anti-polypeptide antisera raised to the polypeptides whose amino acid residue sequences are shown in Table 1 were then screened by the ELISA assay described in Example 3. All of the rabbit antisera so prepared and screened by the ELISA assay immunoreacted with the immunizing polypeptide at titers in excess of 1:2560.

3. ELISA Assays

Antibody molecules contained in antibody compositions and monoclonal antibody compositions were examined for their ability to immunoreact with various polypeptides using an enzyme-linked immunoassay (ELISA) procedure.

One hundred ul of coating solution (0.1M sodium carbonate buffer, pH 9.2) containing polypeptide prepared as described in Example 1a at a concentration of 10 ug per ml coating solution was added to each well of a flat-bottom 96-well microtiter plate, and the plate was maintained overnight at room temperature to permit the polypeptide to adsorb onto the walls of the wells. Thereafter the coating solution was removed by inversion and shaking, the wells were rinsed twice with distilled water and 150 ul of blocking solution [3% bovine serum albumin (BSA; w/v) in PBS]were admixed into each well (solid support) to block excess protein sites.

The wells were maintained for 20 minutes at room temperature and then the blocking solution was removed by shaking. Into each well was admixed 100 ul of a solution containing rabbit anti-peptide antisera, prepared as described in Example 2c and serially diluted in blocking buffer. The resulting solid/liquid phase immunoreaction admixtures were maintained at room temperature for 60 minutes to permit formation of a first solid phase-bound immunoreaction product between the solid phase-bound polypeptide and admixed antibodies. The solid and liquid phases were then separated, the wells were rinsed 5 times with distilled water and excess liquid was removed by shaking.

One hundred ul of a solution containing glucose oxidase labeled goat anti-rabbit IgG (Cooper Biomedical, Malvern, Pa.), diluted 1:1000 in blocking solution, was admixed into each well to form a second solid/liquid phase immunoreaction admixture (labeling immunoreaction admixture). The wells were maintained for one hour at 37 degrees C. to permit formation of a second immunoreaction product between the labeled antibody and any solid phase-bound antibody of the first immunoreaction product and then rinsed 5 times with distilled water to isolate the solid phase-bound label containing immunoreaction products. Excess liquid was then removed from the wells.

A chromogenic substrate solution was freshly prepared before use by admixing (1) 28 mls of a prepared glucose solution containing 2.1% glucose (w/)) in PB [0.1M phosphate buffer (pH 6.0)], said glucose solution having been maintained overnight to allow the glucose to mutarotate, (2) 200 ul of a solution containing 0.1% (w/v) horseradish peroxidase in PB, and (3) 200 ul of an ABTS solution containing freshly prepared ABTS dye (2,2'-azino-di[3-ethylbenzthiazolinesulfonate(6)] diammonium salt; Boehringer-Mannheim, Indianapolis, Ind.) at a concentration of 45 mg per ml PB. 100 ul of the chromogenic substrate solution were then admixed into each well to form a color developing-reaction admixture. After maintaining the developing-reaction admixture in the dark for 1 hour at room temperature, the O.D. of the solution admixture was measured directly in the well using a multiskan microtiter plate reader (Bio-Tek Instr., Winooski, Vt.) with a 415 nm filter.

The results of the above ELISA procedure were expressed as a dilution of the antibody composition that provided approximately 50% of the maximum O.D. that the chromogenic substrate solution produced when using undiluted, positively reacting antigen. Antibody molecules contained in those compositions were considered as having the capability to immunoreact with a solid phase polypeptide if the dilution to achieve 50 maximal O.D. was greater than 1:4.

4. Polypeptide-Ligand Affinity Isolation of Rabbit Polyclonal Antisera

To increase the specificity of rabbit anti-polypeptide antisera, these antisera were affinity isolated using solid phase polypeptide ligands as described herein.

Five milligrams of polypeptide, prepared as described in Example 1, was dissolved in water and subsequently coupled to AH-Sepharose 4B (Pharmacia) according to the manufacturer's instructions to form a polypeptide-agarose solid support. A column having a 3 ml bed volume was prepared using polypeptide-agarose solid support and equilibrated by rinsing with NET buffer (150 mM NaCl, 1 mM EDTA, 20 mM Tris-HCl, pH 7.5). About 10 mls of a rabbit anti-polypeptide antiserum, prepared as described in Example 2c, was applied to the equilibrated column and the column was then washed with 30 column volumes of NET buffer. Thereafter 100 mM citrate buffer (pH 3.0) was applied to the column and the eluate was collected in fractions. The O.D. of the fractions was measured at 280 nm, the peak-containing fractions were determined and pooled to yield an antibody containing pool. The pH of the pool was measured and adjusted to 7.0 using Tris-base and was then dialyzed against PBS to yield a solution containing affinity purified rabbit antibody molecules.

The resulting affinity purified rabbit antibody molecule containing solution represents a substantially isolated antibody because greater than 50% of the antibody molecules contained in the solution have the capacity to immunoreact with an HPV latent protein.

Each rabbit anti-polypeptide antiserum affinity-isolated by the above procedure was isolated using the same polypeptide as was used in the preparation of the immunogen that raised that particular antiserum. The rabbit anti-polypeptide antisera that was affinity-isolated (AI) by this method includes rabbit anti-polypeptide 235 (rabbit anti-235), hereinafter referred to as rabbit AI anti-235, rabbit AI anti-236, rabbit AI anti-245 and rabbit AI anti-247.

5. Western Immunoblot Detection of Latent Papillomavirus Proteins Using Polyclonal Anti-Polypeptide Antibodies Using Western immunoblot assays, HPV-containing tissue culture cell lysates and various biopsy samples were prepared and examined for the presence of latent human papillomavirus proteins.

The human cervical carcinoma cell lines, C-33A (HTB-31), HT-3 (HTB-32), Hela (CCL2), CaSki (CRL 1550), MS 751 (HTB 34) and SiHa (HTB 35) were obtained from the American Type Culture Collection (ATCC; Rockville, Md.), have the ATCC designations indicated in parenthesis after their names, and were cultured using ATCC recommended media and methods.

Cells grown in monolayer culture were harvested and washed twice in PBS-EDTA (PBS containing 0.02% EDTA), pelleted to recover the washed cells and the PBS-EDTA was removed to yield a packed cell pellet. The packed cell pellet was weighted, resuspended by vortexing in PBS at 4° C. at a concentration of 0.1 gms packed cell pellet per 0.5 mls PBS, and lysed by the addition of 0.5 mls of 2XSB (i.e., a buffer prepared having twice the concentration of sample buffer) to yield cell lysates. Sample buffer (SB) contains 2% SDS, 50 mM dithiolthreitol, 10% glycerol, 125 mM Tris-HCl pH 6.8 and 1 mM phenyl methyl sulfonyl flouride (PMSF).

Tissue biopsies of condyloma, obtained from Dr. Z. Bekassy (Department of Gynecology, Lund University Hospital, Lund, Sweden), were weighed, minced and suspended in SB at a concentration of 0.1 mg per ml. The minced suspension was disrupted by three strokes in a loose fitting pestle of a dounce homogenizer, and then sonicated for 1.5 hours in a waterbath sonicator. The sonicated suspension was frozen to −70 degrees C. and thawed through 4 cycles of freeze-thaw, and the resulting suspension was centrifuged at abut 12,000 xg in a microcentrifuge to remove tissue debris. The resulting supernatant was retained to yield a condyloma tissue lysate.

Cell lysates were subjected to SDS-polyacrylamide gel electrophoresis (SDS-PAGE) on a 7.5% slab gel using the discontinuous buffer system described by Laemmli, *Nature*, 226:680–685 (1970) as modified by Blake et al., *Infect. Immun.*, 33:212–272 (1981), which method is hereby incorporated by reference, using 100 microliter (ul) of cell lysate per gel lane, flanked on either side by a lane containing prestained molecular weight marker proteins (Bio-Rad Laboratories, Richmond, Calif.). The proteins present in the marker preparation include: lysozyme, 14.4 kd; trypsin inhibitor, 21.5 kd; carbonic anhydrase, 31 kd; ovalbumin, 42.7 kd; bovine serum albumin, 66.2 kd; phosphorylase b, 97.4 kd; beta-galactosidase, 116.25; and myosin, 200 kd, all in units of one thousand daltons.

After electrophoresis and electroblotting using a Bio-Rad transfer unit (BioRad, Richmond, Calif.) onto nitrocellulose, as described by Towbin et al., *Proc. Natl. Acad. Sci. USA*, 76:4350–4354 (1979) which method is hereby incorporated by reference, the blot was blocked with a solution of BLOTTO [5% powdered nonfat milk in PBS containing 0.025% antifoam A (sigma Chemical Corp. St. Louis, Mo.)] by immersion of the blot into BLOTTO for 1 hour with agitation. Blocked blots were then maintained in BLOTTO containing rabbit anti-polypeptide antisera or AI rabbit anti-polypeptide antisera as indicated at a dilution of 1:100 in BLOTTO for 2 hours at room temperature to allow an immunoreaction product to form between the admixed antibody compositions and the latent papillomavirus protein present as solid phase on the blots. Thereafter the blots were washed in BLOTTO three times for about 1 minute, 20 minutes and 20 minutes, respectively, to remove unbound anti-peptide antisera. The washed blots were then maintained for 30 minutes in BLOTTO containing alkaline phosphatase conjugated goat anti-rabbit IgG (Sigma) diluted to 1:1000 to allow a second immunoreaction product to form between the second admixed antibody and the first formed immunoreaction product present on the solid phase of the blot. The blot was then washed in PBS-T (PBS containing 0.5% Tween 20) once for 5 minutes and 4 times for 30 minutes each to remove the unbound second admixed antibody. The washed blot was then maintained in a solution of chromogenic substrate containing developer for about 4 hours at room temperature to visualize the immunoreaction products present on the blot.

Developer solution was prepared by admixing 5 ml 1.5M Tris (pH 8.8), 45 ml water, 5 mg nitro blue tetrazolium, 0.2 ml 1M $MgCl_2$ and 2.5 mg 5-bromo-4-chloroindoxylphosphate.

Results using the Western immunoblot assay to detect latent papillomavirus protein are shown in FIGS. 2 and 3.

For instance lanes 1–4 of FIG. 2 illustrated that the diffuse protein having a molecular weight of about 112 kd was detected in SiHa and HeLa cell lysates, but not in CaSki or C-33A cell lysates, using polyclonal rabbit anti-236 antisera. The same 112 kd diffuse protein was also detected by the formation of an immunoreaction product on immunoblots using rabbit anti-245 antisera.

Lanes 6 and 7 of FIG. 2 show that the HPV 54 kd filamentous protein was detected by immunoblotting cell lysates of condyloma biopsy tissues with rabbit anti-236 antisera. The HPV 48 kd filamentous protein was also detected in one of the condyloma biopsy cell lysates using rabbit anti-236 antisera (FIG. 2, lanes 6) but not in the other condyloma lysate (lane 7). The 48 kd filamentous protein has also been detected by immunoreaction on blots using rabbit anti-235 rabbit anti-245 and rabbit anti-247.

FIG. 3 demonstrates that a polyclonal antisera raised against polypeptide 236 can be used as a type-specific reagent for distinguishing between HPV type 16 and HPV type 18 infections. As shown in FIG. 3, the 54 kd and 58 kd filamentous proteins were both detected by immunoblotting CaSki cell lysates (lane 2) but were not detected tin HeLa cell lysates (lane 1) using rabbit anti-236 antisera.

The 51 kd nuclear protein was detected by immunoblotting CaSki cell lysates with affinity isolated rabbit anti-245.

The above results demonstrate that antipeptide antisera raised to polypeptides deduced from E region ORFs of papillomaviruses have the capacity to immunoreact with papillomavirus latent proteins. In some cases an anti-polypeptide antisera has the capacity to immunoreact with a latent protein produced by one but not another HPV type, i.e., a type-specific antisera.

6. Preparation of Hybridomas and Anti-Polypeptide Monoclonal Antibodies a. Mouse Immunizations All hybridomas were produced using spleen cells from immunized 129 $G_{IX}{}^+$ mice obtained from the SCRF Vivarium (La Jolla, Calif.) having an age of about 3 weeks at the beginning of immunization.

Each of the polypeptides listed in Table 1 was KLH-conjugated and used as an immunogen to produce the hybridomas described herein.

Each mouse to be immunized with a particular polypeptide was first injected intraperitoneally (IP) with a suspension that contained an emulsified admixture of about 62.5 ul of a KLH-conjugated polypeptide solution, prepared as in Example 2b, 0.43 ml PBS and 0.5 ml complete Freund's adjuvant (CFA). About two weeks later each mouse received an injection IP of a suspension containing about 32 ul of the same KLH-conjugated polypeptide solution as previously received, 0.47 ml PBS and 0.5 ml alum suspension (aluminum hydroxide at 10 mg/ml in PBS). About 7 to 10 days after the second injection, mouse antisera was collected by eyebleed and the titer of the antisera was determined using the ELISA procedure described in Example 3 except using the modifications described hereinbelow.

After the microtiter wells were coated with the same polypeptide as used in the mouse immunization, the wells were blocked as described and then serial dilutions of mouse eyebleed antisera diluted in blocking buffer were admixed and the admixture was maintained as described. Where glucose oxidase conjugated antibody is required in the ELISA method, goat anti-mouse IgG conjugate was used in place of anti-rabbit IgG (Cooper Biomedical). If the eyebleed titer was determined to be less than 1:3200 to achieve 50% maximal OD at 415 nm, then an additional injection was administered to the mouse 2 weeks after the second injection containing the same inoculum as for the second.

About one month after the titer of the eyebleed reaches greater than 1:3200, the mouse was given a final injection of a suspension containing about 32 ul of the same KLH-conjugated polypeptide solution as previously received and 0.47 ml PBS, administered intravenously (IV) into a tail vein.

b. Hybridoma Fusion

Mouse spleenocytes were harvested from the mouse immunized in Example 6a about 3 days after the final injection and fusion with myeloma cells was conducted as described herein. About $1 \times 10^8$ spleen cells (ATCC CRF 1581) from each mouse were admixed with about $2 \times 10^7$ SP2/0-Ag 14 myeloma cells in a fusion medium comprising 40% PEG (Boehringer-Mannheim, Indianapolis, Ind.). After cell fusion, the resulting hybridoma cells were seeded into 96 well microtiter plates, cultured in HAT medium (hypoxanthine, aminopterin and thymidine) as is well known, and the surviving hybridoma cultures resulting therefrom were screened for the ability to produce antibody molecules that immunoreact with the immunizing polypeptide using the modified ELISA procedure described in Example 6a except that hybridoma culture supernatants were used in place of the mouse eyebleed antisera.

Hybridoma culture supernatants screened for the presence of anti-polypeptide antibody molecules in the ELISA assay were considered positive if the optical density (O.D.) at 414 nm of 1:2 diluted culture supernatant was greater than four times the O.D. obtained for control culture medium. A typical fusion was plated onto thirty 96-well microtiter plates and yielded from 10 to 60 hybridoma cultures per fusion that immunoreacted with the immunizing polypeptide in the ELISA assay.

Antibody molecules produced by a particular hybridoma selected by th foregoing screening methods are referred herein by characters that indicate 1) the polypeptide used to immunize the mouse that donated spleen cells to a particular fusion, and 2) the 96 well culture plate, row and well number from which the particular HAP medium resistant hybridoma cell was isolated. The specific referring character is listed herein as one word, where the number preceding the colon is the polypeptide designation and the symbols following designate the microtiter well (e.g., 247:11D12).

Isolated hybridomas are shown in Table 5 below.

TABLE 5

| Immunizing Polypeptide | Hybridomas | # Total Hybridomas Produced |
|---|---|---|
| 235 | 1G5,2A5,2C9,2F9,2G7 3C5,3E9,3F12,3G5,4F5, 4F7,4G12,5A6,5D3,5D7, 5G11,6D11,6G9,6H4,7B8,7E9, 7F12,7G1,8G4,8G10,8H10, 9C7,9F5,9G10,11E1,B9 | 31 |
| 236 | 1C4,1C12,1F6,2A11,2D5, 2F11,3G4,4D1,6H5,8C11, 8G6,9C11,9H5,10C3,11C4, 11G2,11G6,11H8,12D5 | 31 19 |
| 238 | 2D4,4D4,5A10,8E9,8G10, 10C10,10C11,10E10 | 8 |
| 245 | 2A1,2F11,4E3,4F7,8D4, 11E3,13D11,14C6,15F8,15F10, 17C6 | 11 |
| 246 | 1D10,2H4,3F2,4GH,7D8,9E1 | 6 |
| 247 | 1B8,1C2,1F11,2C9,2G12, 4D11,5F7,5F8,7G7,9E3, 9G2,9G6,9G9,10F7,11D11, 12B11,12C10,13E11,14D10, 17D10 | 20 | c. FPLC Purification of Monoclonal Antibodies

A monoclonal antibody composition was prepared by harvesting the ascites fluid of a mouse that had been injected IP with a hybridoma culture and maintained by methods well known. Two ml of the resulting ascites fluid was centrifuged for 15 min at 12,000 xg, the supernatant was collected and filtered through a 0.2 u Acrodisc filter (Gelman) to yield filtered Ascites fluid.

A Superose 6 and a Superose 12 column (Pharmacia) were connected in series on an FPLC apparatus and equilibrated with PBS for 60 min at a flow rate of 0.5 ml/min. Five hundred ul of the filtered ascites fluid were applied to the equilibrated columns and chromatographed at a flow rate of 0.4 ml per min using PBS. The resulting eluant was monitored for optical density (O.D.) at 280 nm and 1 ml fractions of the eluant were collected. Fractions were assayed by the ELISA procedure for the presence of anti-polypeptide antibody molecules using the immunizing polypeptide as described in Example 6b. Typically two fractions were determined to contain the majority of the anti-polypeptide antibodies and the two 1 ml fractions were then pooled to yield an FPLC purified monoclonal antibody solution having a anti-polypeptide titer greater than 1:2560 as determined by ELISA described in Example 6b.

By this procedure monoclonal antibodies 247:4D11, 235:B9 and 245:11E3 were FPLC purified, having a known protein concentration based on the O.D. 280 measurements taken.

Each of the resulting FPLC purified monoclonal antibody molecule containing solutions represent a substantially pure antibody because greater than 50% of the protein contained in the solution is composed of protein molecules that form antibody combining sites.

7. Western Immunoblot Detection of Papillomavirus Latent Proteins Using Anti-Polypeptide Monoclonal Antibodies Monoclonal antibodies prepared as described in Example 6 were used to detect human papillomavirus latent proteins present in HPV-containing tissues by the same Western immunoblot procedures described in Example 5 with the exceptions noted herein.

An electroblotted and blocked nitrocellulose blot prepared as in Example 5 was admixed with a solution containing FPLC purified antibody solution, prepared as described in Example 6c, diluted to a concentration of 32 ug per ml of BLOTTO for 247:4D11 or to a concentration of 25 ug per ml of diluted BLOTTO (to 2% milk) for 235:B9, and maintained in that solution as previously described to allow an immunoreaction product to form. As before the blot was washed, and then was maintained for 45 minutes in a solution of BLOTTO containing rabbit anti-mouse antibodies (Cooper Biomedical) diluted to a concentration of about 1:500 to allow the formation of an immunoreaction product. Thereafter the blot was washed in BLOTTO 3 times for 1, 20 and 20 minutes and then maintained in a BLOTTO solution containing alkaline phosphatase conjugated goat anti-rabbit IgG as previously described. Subsequent washes and development were also as before.

The resulting immunoblot, shown in FIG. 4, demonstrates the detection of the 54 kd and 48 kd filamentous proteins, in CaSki cell lysates (Lane 4) when using the monoclonal antibody 247:4D11. Also observed in CaSki cell lysates is an additional HPV-specific protein having a molecular weight of about 58 kd. The 58 kd protein is believed to be a product of cellular processing (glycosylation) of the 54 kd filamentous protein. Monoclonal antibody 247:4D11 also immunoreacts with the 54 kd filamentous protein present in HeLa cell lysates, but does not immunoreact significantly with the shown preparation of SiHa or HT-3 cell lysates. (lanes 2 and 5, respectively).

By the above immunoblotting methods monoclonal antibodies were demonstrated to immunoreact with all the papillomavirus latent proteins. For example, the 54 kd filamentous protein was detected by immunoblotting HeLa, CaSki and SiHa cell lysates using monoclonal antibodies 235:B9 or 247:4D11. The 48 kd filamentous protein was similarly detected in CaSki cell lysates using these same monoclonal antibodies. The nuclear protein was detected by immunoblotting CaSki cell lysates using monoclonal antibody 245:11E3. The diffuse protein was detected by immunoblotting HeLa and SiHa cell lysates using monoclonal antibodies 235:B9, 238:8E9, 247:10F7 and 247:11D11.

8. Immunohistochemical Detection of Latent Papillomavirus Proteins a. Detection in HPV-Containing Tissue Culture Cells Cervical carcinoma cell lines HT-3, MS751, C-33A, SiHa, HeLa, and CaSki were cultured as described in Example 5. Semi-confluent monolayer cultures were selected, rinsed with PBS to remove excess culture media and air dried for 10 minutes. Air dried cultures were then fixed by flooding the culture with cold (−20 degrees C.) acetone for 5 min. The fixed cultures were then maintained in 3% hydrogen peroxide for 15 minutes followed by fifty rapid immersions into and out (i.e., dips) of PBS at room temperature. The cultures were then maintained first in PBS for 2 minutes and then maintained in a continuously rocking PBS solution containing 8% normal horse serum and 0.01% thimerosal for 1 hr at room temperature to form non-specific protein binding site-blocked samples.

The blocked samples were maintained at room temperature for 60 minutes with a solution containing an anti-peptide antibody composition to form an immunoreaction product containing the admixed antibody and the blocked sample. As described below, several different antibodies were used in these assays at different dilutions. Thereafter the immunoreacted sample was dipped 20 times in PBS, maintained for 2 minutes in PBS, (i.e., 20 dips plus 2 min) and this was repeated twice (i.e., 3 times, 20 dips each plus 2 min). The sample was then maintained in a solution of 0.5% BLOTTO (0.5% non-fat powdered milk, 0.01% thimerosal, 0.025% antifoam A in PBS) containing biotinylated horse anti-mouse IgG (Vector Labs, Burlingame, Calif.) at a concentration of 7 ug per ml for 45 minutes at room temperature to allow the formation of a second immunoreaction product between the admixed biotinylated IgG and the bound mouse antibodies present on the sample. Thereafter the sample was rinsed in PBS three times, 20 dips each plus 2 minutes, and then maintained at room temperature in NHT buffer (0.3 M NaCl, 20 mM Hepes, pH 6.5, 0.01% thimerosal) containing avidin D-peroxidase (Vector labs) at 12 ug per ml for 30 minutes to allow the avidin reagent to complex with the biotin present in the second immunoreaction product. Thereafter the sample was rinsed in PBS three times, 20 dips each plus 2 minutes, and then maintained in AEC buffer, prepared by admixing (1) 4 mls dimethyformamide containing 50 mg of aminoethyl carbazole (Sigma), (2) 80 ul hydrogen peroxide, and (3) 200 ml 100 mM sodium acetate buffer pH 5.5 for 10 minutes at room temperature to allow the color-developing reaction to occur on the sample. After development, the samples were shaken to remove excess liquid, rinsed in water and then maintained in Mayer's hematoxylin stain (Sigma) for three minutes followed by a water rinse. The stained sample was then mounted in 50% glycerol in water and viewed by light microscopy.

Results of immunohistochemical staining (immunostaining) of HPV-containing cell lines is shown in Table 6.

TABLE 6

| | Immunostaining of HPV-Containing Tissue Culture Cell Lines[1] | | |
|---|---|---|---|
| | Antibody Composition[2] | | |
| Cell Line | 235:B9 | 245:11E3 | 247:4D11 |
| HeLa | +++ | + | +++ |
| CaSki | +++ | +++ | +++ |
| SiHa | +++ | --- | +++ |
| MS751 | +++ | +++ | +++ |
| HT-3 | --- | --- | --- |
| C33-A | --- | --- | --- |

[1] A significant and positive immunoreaction was determined by the presence of the characteristic rust colored staining pattern (+++) as compared to the blue-grey color of the hematoxylin counterstain that predominates in the absence of antibody dependent peroxidase staining (−). In some cases, a weak immunoreaction was observed (+).
[2] Monoclonal antibody 235:B9 was immunoreacted with the blocked sample using a solution containing FPLC purified antibody, prepared as described in Example 6c, at a concentration of 25 ug per ml of 0.2% BLOTTO (0.2% non-fat powdered milk, 0.01% thimerosal, 0.025% antifoam A, in PBS). Monoclonal antibody 245:11E3 was immunoreacted with the blocked sample using a solution of ascites fluid that was prepared as described in Example 6c and diluted 1:40 in 10% normal horse serum (10% v/v in PB S). Monoclonal antibody 247:4D11 was immunoreacted with the blocked sample using a solution containing FPLC purified antibody at a concentration of 100 ug per ml of 10% normal horse serum.

The results in Table 6 demonstrate the ability of a monoclonal antibody of this invention to immunoreact with latent HPV proteins in an immunostaining format using HPV infected cell lines. The specificity for papillomavirus latent proteins is demonstrated by the ability of these antibodies to immunoreact with cells known to contain HPVs (HeLa, CaSki, SiHa and MS751) but not with cells that do not contain HPV (HT-3 and C33-A).

b. Detection of Papillomavirus Latent Protein in Tissue Samples

Formalin-fixed, paraffin-embedded tissue biopsies of human cervical carcinoma and human condyloma were obtained from Dr. Carpenter (UCSD Medical Center, San Diego, Calif.), Dr. J. Robb (Dept. of Pathology, Green Hospital, La Jolla, Calif.) and Dr. W. Lancaster (Georgetown University, Washington, D.C.). Papanicolaou ("pap") smears were obtained from Dr. J. Willems (OB/GYN, Scripps Clinic, La Jolla, Calif.). These tissue samples were subjected to the same immunohistochemical staining procedure described in Example 8a with exceptions as hereby noted.

Formalin-fixed, embedded tissues were first deparaffinized in xylene by 50 dips followed by a 2 minutes soak in xylene. Thereafter the fixed tissue was dipped 50 times into 95% ethanol followed by a 2 minute soak, then dipped 50 times into 80% ethanol followed by a 2 minute soak, then dipped into 50% ethanol 50 times followed by a 2 minute soak, and finally dipped 50 times in PBS followed by a 2 minute soak to form a rehydrated sample. Thereafter the rehydrated sample was processed as described in Example 8a beginning with the step of maintaining the sample in 3% hydrogen peroxide solution.

Pap smear-containing slides were air dried for 10 minutes, and then fixed by maintenance in 67% acetone/33% methanol for 10 minutes at −20 degrees C. The fixed pap smears were then processed as described in Example 8a beginning with the step of maintaining the sample in the 3% peroxide solution.

Results of immunostaining various tissue biopsy samples using monoclonal antibodies of the present invention are shown in Table 7.

TABLE 7

Immunostaining of HPV-Containing Tissue Biopsies[1]

| Tissue | No. Samples | Antibody Composition[2] | | |
|---|---|---|---|---|
| | | 235:B9 | 245:11E3 | 247:4D11 |
| Pap Smear[3] | | | | |
| Condylomatous | 3 | 3/3 | N.T. | N.T. |
| Not infected | 1 | 0/1 | N.T. | N.T. |
| Biopsy[4] | | | | |
| Cervical Dysplasia | | | | |
| HPV Type 16 | 14 | 14/14 | 14/14 | 11/11 |
| HPV Type 31 | 3 | 3/3 | 2/2 | 2/2 |
| HPV Type 11 | 2 | 2/2 | 0/2 | 0/2 |
| Untyped | 2 | 2/2 | N.T. | 1/1 |
| Cervical Cancer | 8 | 5/8 | 5/8 | 2/2 |
| "Normal" epithelium | 2 | 1/2 | 0/1 | 0/2 |
| Uninfected epithelium | 1 | 0/1 | 0/1 | 0/1 |

[1]Results of immunostaining are reported as the number of tissues that tested positive over the total number of samples tested. A positive reaction was scored if the staining was significant as described in note 1 of Table 6.
[2]Monoclonal antibodies 235:B9, 235:11E3 and 247:4D11 were immunoreacted using the conditions described in note 2 of Table 6.
[3]Pap smears obtained from patients having colposcopically verified cervical condylomas were designated condylomatous. The pap smear designated "not infected" was derived from a verified virgin, believed to have had no risk of exposure to genital HPV infection.
[4]Biopsy samples included biopsies of cervical dysplasia that were screened for the presence of a particular HPV type by nucleic acid hybridization [DeVilliers et al., Lancet, ii:703 (1987)] where indicated. Cervical cancer biopsies were screened having unknown HPV status. Two seemingly normal epithelium biopsies from surgery were screened, having unknown HPV status. A control uninfected epithelium biopsy was obtained from a six-year old female believed to have no risk of exposure to genital HPV infection.

The results in Table 7 demonstrate the ability of monoclonal antibody molecules to immunoreact with HPV latent proteins present in biopsy tissue samples. These samples showed 100% positive reactivity with no false negatives when using 235:B9 on samples known by independent means to contain latent HPV infection.

The results in Table 7 also demonstrate that certain monoclonal antibodies have the ability to immunoreact with a latent protein produced by one but not another HPV type, i.e., a type specific antibody molecule. For example, whereas monoclonal antibody 235:B9 immunoreacted by immunostaining with the HPV-typed dysplasia tissues having an 11, 16 or 31 type designation, the monoclonal antibodies 245:11E7 and 247:4D11 immunoreacted with HPV type 15 and type 31 containing dysplasias but did not immunoreact with type 11 containing dysplasias.

In addition, detection of HPV latent proteins by immunostaining indicates the cellular localization of the latent proteins, thus providing additional characterization of these proteins. For example, the monoclonal antibody 247:4D11 produced an immunostaining pattern on CaSki cells or on various HPV-containing biopsy tissues that was distributed over cytoplasmic filament-associated components of the cell. Therefore, the 46 kd, 54 kd and 58 kd proteins, detected by immunoblotting with monoclonal antibody 247:4D11 as shown in Example 7, have been further characterized as being "filamentous" type latent proteins based on their distribution in immunostained cells. A similar filamentous staining pattern was observed using monoclonal antibody 235:B9 to immunostain HPV-containing pap smears, biopsy samples and tissue culture cells.

Monoclonal antibody 245:11E3 produced a characteristic immunostaining pattern in CaSki cells that was localized to the nuclei. Thus, the 51 kd protein, detected by immunoblotting with this monoclonal antibody as described in Example 7, has been further characterized as being a "nuclear" type latent protein.

Monoclonal antibodies 238:8E9, 247:10F7 and 247:11D11 each produced a characteristic immunostaining pattern in HeLa cells and SiHa cells that was localized in a diffuse manner throughout both the nucleus and the cytoplasm of the stained cells. Because these monoclonal antibodies detected the 112 kd protein in the immunoblotting assay described in Example 7. The 112 kd protein has been further characterized as being a "diffuse" type latent protein.

9. Detection of Anti-HPV Latent Protein Antibody Molecules in Human Blood

Antisera from patients diagnosed as having latent HPV infection, in the form of histologically confirmed condyloma lesions, were obtained from Drs. R. Robb and J. Willems (Scripps Clinic, La Jolla, Calif.).

Following an ELISA procedure similar to that described in Example 3, these antisera were evaluated for the ability to bind to polypeptides 237, 245 and 246, with the following exceptions as noted.

Fifty ul of coating solution containing 1 ug of polypeptide 237, 245 or 246 were added to the wells of a microtiter plate, and maintained at 4 degrees C. overnight to allow the polypeptide to adsorb to the walls of the wells. Thereafter the wells were rinsed as before and blocked by adding and maintaining NGS Buffer (10% normal goat serum in PBS) for 90 minutes at 37 degrees C. The wells were then emptied by inversion and shaking to remove the excess liquid, and were dried by maintaining the wells at 37 degrees C. for 1 hour to form dried plates.

One hundred ul of solution containing a patient antisera diluted in NGS buffer was admixed to each to form an immunoreaction admixture, and the admixture was maintained at 37 degrees C. for 1 hour to allow the antibodies in the antisera to immunoreact with the polypeptides adsorbed onto the well walls and form a polypeptide-containing immunoreaction product. The wells were then washed 5 times with PBS-T (0.5% Tween 20 in PBS) to remove the unbound antisera, and the excess liquid was removed by shaking.

One hundred ul of a solution containing horseradish peroxidase labeled monoclonal anti-human immunoglobulin IgA conjugate (Janssen, Piscataway, N.J.) diluted 1:5000 in NGS buffer was admixed into each well and maintained for 1 hr at 37 degrees C. to permit formation of a second immunoreaction product between the bound human antibodies and the added labeled conjugate. The added solution was then removed, the wells rinsed as before and excess liquid was removed by shaking.

A peroxidase substrate solution was freshly prepared by admixing (1) 50 ml developing buffer [0.12M Citric Acid, 0.26M dibasic sodium phosphate (pH 5.0)], (2) 1 ml OPD (1 mg orthophenylenediamine per ml water), and (3) 25 ul 30% hydrogen peroxide. One hundred ul of the peroxidase substrate solution were then admixed into each well to form a color developing-reaction admixture. After maintaining the developing-reaction admixture in the dark for 20 minutes at room temperature, the O.D. of the solution admixture was measured using a multiskan plate reader equipped with a 492 nm filter.

Antisera from 6 different condylomatous patients when tested in the above ELISA procedure, demonstrated elevated levels of immunoglobulin IgA antibody molecules that immunoreacted with both polypeptides 237, 245 and 246. In contrast antisera from three healthy control patients failed to immunoreact with polypeptides 237, 245 or 246 Further, antisera from a patient with HPV type 11 condyloma failed to immunoreact with either polypeptide.

Antisera from a HPV-carrying patient was also show to immunoreact with HPV latent proteins using an immunoblotting format.

Antisera that immunoreacted in the abov ELISA format using polypeptide 245 was affinity isolated as described in Example 4. Affinity isolated anti-polypeptide 245 antisera (AI anti-245) was then used in the immunoblot assay described in Example 5 on blots that contained cell lysates prepared from CaSki, SiHa, HeLa, C-33A and HT-3 cells when this immunoblot assay was conducted using alkaline phosphatase labeled monoclonal anti-human immunoglobulin IgA antibodies in place of the goat anti-rabbit IgG antibodies as described for immunoblotting in Example 5, a 58 kd HPV latent protein was detected in the CaSki cell lysates only. These results indicate that the presence of human anti-HPV latent protein antibodies can be demonstrated using the immunoblotting format.

10. Isolation of a Papillomavirus Latent Protein

One hundred mg of each of Macrosphere Amino 300 A° beads (Alltech Associates, Deerfield, Ill.) were dispersed in 15 mls of 50 mM phosphate buffer (pH 7.0), and the dispersion was degassed. The beads were recovered from the degassed dispersion by centrifugation and the resulting pellet was recovered and resuspended in 13.5 ml of 50 mM phosphate buffer (pH 7.5) to form a degassed bead suspension. While stirring the degassed bead suspension, 1.5 ml of 25% aqueous glutaraldehyde (FM Science, Cherry Hill, N.J.) was admixed and the stirring continued for 3 minutes to form glutaraldehyde coupled beads. Water was then added to the coupled beads while stirring to bring the final volume up to 50 ml, the beads were collected by centrifugation and washed in 50 ml water three times to form activated beads.

An amount of rabbit anti-polypeptide 236 antisera, prepared as described in Example 2c and containing about 500 mg of total protein, was diluted with an equal volume of PBS and centrifuged at 12,000 rpm at 4 degrees C. for 15 min. in a JA-200 rotor (Beckman). The resulting supernatant was extracted with an equal volume of chloroform, and the aqueous phase was dialyzed overnight against buffer A (100 mM Tris-HCl, pH 8.0) to form dialyzed rabbit antisera.

About 9 mls of dialyzed rabbit antisera was applied to a PD-10 column (Pharmacia Fine Chemicals, Piscataway, N.J.), pre-equilibrated with 25 mls of buffer A. Of the eluant that exited the column, the first 2.5 mls were discarded and the remaining eluant was retained. Thereafter four mls of buffer A were then added to the column and the resulting eluant was again retained and admixed with the previously retained eluant. The admixture was passed through a 0.2u nitrocellulose acrodisc filter (Gelman Sciences, Ann Arbor, Mich.) to form a filtered rabbit antisera.

The filtered rabbit antisera was applied to a Mono Q anion exchanger column equipped on an automated FPLC apparatus (Pharmacia) using buffer A as the equilibrating buffer. The column was then washed in buffer A and then an elution gradient was applied comprising a 0–30% gradient of buffer B (0.5M NaCl in buffer A). The resulting gradient-eluted fractions were monitored for anti-polypeptide antibody immunoreactivity as measured in the ELISA and the assay described in Example 3antibody-containing fractions were pooled to form an FPLC purified anti-polypeptide 236 antibody solution (FPLC anti-236).

One ml of FPLC anti-236 determined by O.D. 280 to have a concentration of 6 mg/ml, was admixed with 10 mg activated beads and the admixture was maintained at 4 degrees C. for 60 minutes in continuous agitation. Thereafter the agitated beads were isolated away from the unbound antibody molecules by centrifugation, resuspended in 1 ml of 1M glycine buffer (pH 7.0) nd maintained for 30 minutes at room temperature to block the excess activated sites present on the beads. The blocked beads were then isolated away from the glycine buffer by centrifugation to form anti-236 conjugated beads.

The anti-236 conjugated beads were washed first in 1 ml of 5 mM Citrate buffer, pH 3.0, to elute excess glycine and were then washed twice in 1 ml PBS followed by 2 washes in RIPA buffer (prepared by admixing 2 ml nonidet P-40 (NP40), 2 gm sodium deoxycholate, 0.2 gm SDS, 2 ml 0.5M EDTA and sufficient PBS to make the final volume 200 ml) to form equilibrated anti-236 conjugated beads.

A 0.12 gm packed cell pellet of HeLa cells was prepared as described in Example 5, frozen to −70 degrees C., thawed and then suspended in 1 ml of RIPA buffer. The HeLa cell suspension was then agitated by three strokes with a loose-fitting pestle in a dounce homogenizer, and the agitated suspension was centrifuged at 12,000×g for 15 minutes in a microcentrifuge. The resulting supernatant was collected and admixed with equilibrated anti-236 conjugated beads, and the admixture was maintained for 2 hr at 4 degrees C. in continuous agitation to allow formation of an immunoreaction product between the conjugated antibodies and the latent papillomavirus diffuse protein. The admixture was then placed in a column and the beads contained in the admixture were washed by rinsing the column with 1 ml of RIPA buffer, 1 ml of LB buffer (0.2% NP 40, 20 mM Tris HCL, pH 7.5, 150 mM NaCl), 1 ml of 1M KCl and 1 ml of 2.5 mM $CaCl_2$ in 5% PBS. To the rinsed column was then added 200 ul of 50 mM sodium citrate, pH 3.0, and the eluant collected. Sufficient 1M sodium phosphate buffer (pH 7.5) was added to the eluant to neutralize the citrate buffer to about pH 7.0 and the neutralized eluant was then admixed with sufficient 100% trichloroacetic acid to achieve 15% TCA in order to precipitate the proteins present in the eluant. The protein precipitate was collected and washed with acetone, and the acetone washed protein was then resuspended in SB and analyzed by SDS-PAGE as described in Example 5.

SDS-PAGE analysis of the acetone washed protein isolated from HeLa cells demonstrated a protein having an apparent molecular weight of about 112 kd, that immunoreacted in the immunoblot assay with rabbit anti-245 antisera prepared in Example 2c.

11. Detection of Anti-HPV Latent Protein Antibody Molecules Using HPV 16-Related Nested Polypeptides The polypeptides shown in Table 2, and polypeptides 245 and a control polypeptide 65 were used in an ELISA assay similar to that described in Example 9 to detect anti-HPV latent protein antibody molecules with the following exceptions as noted.

Fifty ul of coating solution containing polypeptide was added to the wells of a 96 well-flat bottom microtiter plate (Immunolon II, Dynatech, Chantilly, Va.), so that each well contains 1 ug of only one of the polypeptides shown in Table 8. The wells were maintained, rinsed and blocked as before. The plates were then dried as before and thereafter 100 ul of patient sera diluted 1/10 in NGS buffer was added to each well to form an immunoreaction admixture, that was maintained and then washed as before.

Immunoreaction product was detected using a horseradish peroxidase labeled monoclonal anti-human Ig-A conjugate (Janssen) diluted 1:3000 in NGS as before. A second set of wells were similarly prepared except that the labeled conjugate was anti-IgG (Ortho Diagnostics, Ontario, Canada) rather than IgA. The resulting colored reaction admixture was measured for optical density at about 490 nm ($OD_{490}$) and the measurements are shown in Table 8.

TABLE 8

Immunoreaction of HPV-Infected Patient Antisera With HPV Type 16 Polypeptides

| | | Patient No. | | | |
|---|---|---|---|---|---|
| | | 1 | | 2 | |
| No. | Polypeptide Sequence | IgA | IgG | IgA | IgA |
| 65[3] | SSEWQRDQFLSQV | .077 | .028 | .081 | .038 |
| 66 | SSTWHWTGHNVKHKSAIVTLTYD | .129 | .049 | .149 | .060 |
| 245 | HKSAIVTLTYDSEWQRDQC | .343 | .047 | .038 | .911 |
| 71 | HKSAIVTLTYDSEWQRDC | .307 | ND[2] | .280 | ND |
| 72 | HKSAIVTLTYDSEWQRC | .126 | ND | .120 | ND |
| 73 | HKSAIVTLTYDSEWQC | .421 | .040 | .329 | 1.012 |
| 74 | HKSAIVTLTYDSEWC | ND | .082 | .436 | .863 |
| 75 | HKSAIVTLTYDSEC | ND | .032 | .396 | 1.361 |
| 79 | KSAIVTLTYDSEWQRDQC | .201 | .021 | .178 | .386 |
| 80 | SAIVTLTYDSEWQRDQC | .360 | .020 | .365 | .796 |
| 81 | AIVTLTYDSEWQRDQC | .303 | .031 | .283 | .287 |
| 82 | IVTLTYDSEWQRDQC | .252 | .045 | .251 | .066 |
| 83 | VTLTYDSEWQRDQC | .123 | .041 | .189 | .065 |
| 84 | TLTYDSEWQRDQC | .090 | .032 | .092 | .049 |
| 85 | LTYDSEWQRDQC | .123 | .034 | .083 | .066 |
| Blank[1] | | .014 | ND | .010 | .028 |

[1]"Blank" indicates that NGS buffer was added in place of a polypeptide.
[2]"ND" indicates not determined.
[3]Polypeptide 65 is a control polypeptide whose sequence was described by Schoolnick et al., in published Application No. EPO 0257754A2.

The results in Table 8 show that all the polypeptides that included either the sequence —LTYDSF—, or in the case of polypeptide 66, the sequence —HKSAIVTLTYD—, immunoreacted more strongly with IgG or IgA present in the patient's antisera than did control peptide 65. Patient 1 was diagnosed as having a type 18 latent HPV infection, and patient 2 was histologically confirmed to have squamous cell carcinoma of the cervix.

These results show that antisera from a HPV-infected patient immunoreacts with HPV type 16-related polypeptides. The results demonstrate that the immunoreaction is dependent on the presence of either —L-TYDSE— or in the case of polypeptide 66 a less well characterized epitope.

12. Determination of the Binding Epitope for An Anti-HPV Polypeptide Monoclonal Antibody Monoclonal antibody 245:11E3 was evaluated for its ability to immunoreact with HPV type 16-related polypeptides following a solid-phase ELISA procedure similar to that described in Example 3, with the following exceptions as noted.

The polypeptides shown in Table 9 were adsorbed onto the walls of each well of a 96-well microtiter plate (one polypeptide species per well), and thereafter the wells were blocked with NHS buffer (10% normal horse serum in PBS) rather than with blocking solution. Thereafter, 50 ul of monoclonal antibody 245:11E diluted serially in two-fold dilutions using NHS buffer was admixed to each blocked well. The admixture was maintained as before and an immunoreaction product was formed. Solid phase bound immunoreaction product was detected using the goat anti-mouse IgG conjugate as described in Example 6a, and the results shown in Table 9 are expressed as a titer needed to obtain 50% maximal OD at 415 nm.

TABLE 9

| Epitope Mapping Of Mab 245:11E3 | | |
|---|---|---|
| No. | Peptide Sequence | Titre |
| 235 | MADPAGTNGEEGTGC | <1:8 |
| 237 | TYDSEWQRDQFLSQVKIPC | 1:512 |
| 245 | HKSAIVTLTYDSEWQRDQC | 1:512 |
| 74 | HKSAIVTLTYDSEWC | 1:512 |
| 75 | HKSAIVTLTYDSEC | 1:512 |
| 76 | HKSAIVTLTYDSC | 1:256 |
| 77 | HKSAIVTLTYDC | 1:128 |
| 78 | HKSAIVTLTYC | <1:8 |

The results in Table 9 indicate that the epitope for HPV type 16-related polypeptide binding to monoclonal antibody 245:11E3 includes the amino acid residue sequence —TYDSE—.

13. Detection of Anti-HPV Latent Protein Antibody Molecules in Human Blood Using a Combination of HPV Type 16-Related Polypeptides HPV type 16-related polypeptides 237, 245 and 246 were included in an ELISA assay similar to that described in Example 9 to detect anti-HPV latent protein antibody molecules in patient's blood, with the following exceptions as noted.

Antisera was obtained from 46 patients diagnosed as having latent HPV infections, in the form of various histologically confirmed condyloma lesions or grades of cervical dysplasia as indicated in Table 10. These antisera were each admixed in individual wells having polypeptide 237, 245 or 246 adsorbed therein and were assayed as described in Example 9 for the presence of anti-HPV latent protein antibody molecules (immunoglobulin IgA) capable of immunoreaction with the adsorbed HPV type 16-related polypeptides. The results are shown in Table 10.

TABLE 10

| Detection of Patient I$_g$A That Immunoreacts With HPV Type 16 Polypeptides[1] | | | | | |
|---|---|---|---|---|---|
| Patient Number | 237 | 245 | 246 | Blank | Histology[2] |
| 1 | .441 | .550 | .273 | .159 | SC CANCER GRADE ⅜ |
| 2 | .273 | .413 | .144 | .066 | CIN2 |

TABLE 10-continued

| Detection of Patient I$_g$A That Immunoreacts With HPV Type 16 Polypeptides[1] | | | | | |
|---|---|---|---|---|---|
| Patient Number | 237 | 245 | 246 | Blank | Histology[2] |
| 3 | .148 | .243 | .095 | .050 | CIN3 |
| 4 | .091 | .211 | .066 | .026 | UTERUS BIOPSY NEGATIVE |
| 5 | .155 | .333 | .099 | .061 | CIN2 |
| 6 | .281 | .349 | .307 | .070 | CIN3 |
| 7 | .150 | .198 | .111 | .133 | CIN2 |
| 8 | .157 | .227 | .077 | .031 | +/− CIN1 |
| 9 | .279 | .615 | .278 | .119 | CIN1 |
| 10 | .271 | .290 | .152 | .073 | +/− CIN1 |
| 11 | .196 | .228 | .083 | .011 | CIN3 |
| 12 | .332 | .271 | .057 | .058 | CIN2 |
| 13 | .528 | .608 | .311 | .041 | CIN1 |
| 14 | .352 | .431 | .253 | .068 | CIN2 |
| 15 | .320 | .318 | .224 | .048 | CIN2 |
| 16 | .947 | 1.052 | .393 | .048 | CIN3 |
| 17 | .159 | .588 | .064 | .008 | CIN3 |
| 18 | .136 | .477 | .078 | .026 | CIN2 |
| 19 | .181 | .390 | .198 | .034 | CIN3 + AM |
| 20 | .515 | .639 | .299 | .096 | CIN2 |
| 21 | .232 | .281 | .138 | .023 | CIN3 |
| 22 | .105 | .271 | .105 | .022 | CIN3 |
| 23 | .517 | .539 | .134 | .120 | CIN1 |
| 24 | .101 | .128 | .037 | .065 | +/− CIN1 |
| 25 | .515 | .654 | .285 | .187 | CIN2 |
| 26 | .349 | .525 | .254 | .146 | CIN2 |
| 27 | .102 | .207 | .068 | .054 | SC CANCER, MICROINVASIVE |
| 28 | .035 | .067 | .026 | .026 | MALE LAB WORKER |
| 29 | .080 | .078 | .018 | .027 | MALE LAB WORKER |
| 30 | .101 | .142 | .107 | .029 | CIN1 |
| 31 | .052 | .007 | .024 | .011 | OB/GYN NO VISIBLE LESION |
| 32 | .005 | .072 | .107 | .000 | OB/GYN NO VISIBLE LESION |
| 33 | .026 | .050 | .000 | .000 | OB/GYN VISIBLE WART |
| 34 | .000 | .027 | .000 | .012 | CIN1 |
| 35 | .020 | .598 | .023 | .023 | OB/GYN NO VISIBLE LESION |
| 36 | .174 | .243 | .022 | .048 | CIN2 |
| 37 | .017 | .066 | .000 | .027 | +/− COM1 |
| 38 | .177 | .361 | .136 | .098 | CIN2 |
| 39 | .216 | .437 | .108 | .037 | CIN2 |
| 40 | .186 | .211 | .145 | .046 | CIN2 |
| 41 | .046 | .141 | .024 | .037 | OB/GYN VISIBLE WART |
| 42 | .000 | .042 | .000 | .019 | OB/GYN VISIBLE WART |
| 43 | .073 | .211 | .064 | .054 | OB/GYN NO VISIBLE LESION |
| 44 | .074 | .114 | .083 | .023 | OB/GYN VISIBLE WART |
| 45 | .007 | .059 | .040 | .044 | OB/GYN VISIBLE WART |
| 46 | .000 | .057 | .000 | .034 | OB/GYN VISIBLE WART |
| 00 | .012 | .000 | .000 | .000 | NO SERUM ADDED |
| 00 | .000 | .000 | .012 | .003 | NO SERUM ADDED |
| 00 | .006 | .010 | .019 | .019 | NO SERUM ADDED |

[1] The results are expressed as OD$_{492}$ for wells having polypeptide 237, 245 or 246 adsorbed per well, and also for control wells having no polypeptide adsorbed (Blank).
[2] Histology is reported for each antisera donor. CIN indicates cervical intraepithelial neoplasia. Borderline CIN (+/− CIN) is usually carrying HPV of some type, CIN1 is mild dysplasia, CIN2 is moderate dysplasia, and CIN3 is severe dysplasia or carcinoma in situ prior to basal cell layer penetration. Other histological characterizations are also noted.

The results in Table 10 indicate that patients harboring latent HPV infections and exhibiting different stages of cervical dysplasia or condyloma contain in their blood IgA antibody molecules that immunoreact with not only one but several different species of HPV type 16-related polypeptide.

Thus the present invention contemplates the use of different species of polypeptide whose sequences are all deduced from one HPV type, in combinations with one another. These different polypeptides can be included in separate wells of the practiced ELISA assay or diagnostic kit, as above, or can be combined together and adsorbed onto a single solid support, such as in a single well. A preferred combination includes polypeptides 237, 245 and 246 in separate wells of a single microtiter plate.

14. Detection of Anti-HPV Latent Protein Antibody Molecules in Human Blood Using a Combination of HPV Type Specific Polypeptides Panels of antisera obtained from patients having latent HPV infections diagnosed histologically at various grades of dysplasia were analysed in an ELISA assay similar to that described in Example 9 with the following exceptions as noted.

Fifty ul of coating solution containing 1 ug of either polypeptide K69, K70, K72 or 245, or containing 1 ug of PV (purified papillomavirus virions isolated by standard virological procedures from moose warts containing conserved virion papillomavirus proteins) as a control, were added to the wells of a 96 well, half area, flat bottom microtiter plate (Costar, Cambridge, Mass.), and maintained as before to adsorb the added material to the walls of the wells. The wells were blocked using NHS buffer rather than NGS buffer. Thereafter 50 ul of patient sera diluted 1:20 in NHS buffer was admixed to each well to form an immunoreaction admixture, and the admixture was maintained at 37 degrees for 2 hours to allow formation of a polypeptide-containing immunoreaction product.

Fifty ul of a solution containing alkaline phosphatase-labeled polyclonal affinity purified anti-human immunoglobulin IgA conjugate (Dakopatts, Copenhagen, Denmark) diluted 1:800 in NHS buffer was admixed into each well and maintained for 2 hrs at 37 degrees to permit formation of a second immunoreaction product between the bound human antibodies and the added labeled conjugate. The added solution was then removed, the wells rinsed as before using NHS buffer and excess liquid was removed by shaking.

Fifty ul of a PNPP substrate solution [p-nitrophenyl phosphate; SIGMA Chemical Corp. St. Louis, Mo.; at a concentration of 1 mg per ml of diethanolamine buffer, 9.8% (V/V), pH 9.5, containing 0.01% MgCl] were then admixed into each well to form a color developing-reaction solution. After maintaining the admixture for 45 minutes at room temperature, the O.D. of the solution was measured using a multiskan plate reader equipped with a 405 nm filter.

The results measuring immunoglobulin IgA antibody molecules is shown in Table 11.

TABLE 11

Type-Specific Detection Of $I_gA$ In HPV-Infected Patient Antisera

| Patient Number | Histology[1] | HPV Type Specific Polypeptide | | | | |
|---|---|---|---|---|---|---|
| | | PV[2] | 16[3] | 6[4] | 18[5] | 33[6] |
| 1 | SC CANCER | 0 | .614 | 0 | 0 | .025 |
| 2 | CIN2 | 0 | .277 | N.D. | 0 | 0.005 |
| 3 | CIN3 | .128 | .622 | .134 | 0 | .057 |
| 4 | NORMAL | .048 | .154 | .052 | 0 | .037 |
| 6 | CIN3 | .071 | .638 | .182 | 0 | .153 |
| 7 | CIN2 | 0 | .018 | 0 | 0 | .005 |
| 8 | +/− CIN | .045 | .273 | .016 | 0 | .049 |
| 10 | +/− CIN | .057 | .696 | .099 | 0 | .046 |
| 11 | CIN3 | 0 | .086 | 0 | 0 | 0 |
| 12 | CIN2 | 0 | .524 | 0 | 0 | .027 |
| 13 | CIN1 | 0 | .156 | .014 | 0 | .039 |
| 14 | CIN2 | .023 | .462 | .115 | 0 | .072 |
| 15 | CIN2 | 0 | .358 | .110 | 0 | .070 |
| 17 | CIN3 | .012 | .088 | .050 | 0 | .023 |
| 18 | CIN2 | 0 | .362 | .026 | 0 | .003 |
| 20 | CIN2 | .020 | .342 | .079 | .052 | .064 |
| 21 | CIN3 | .036 | .143 | .017 | 0 | .022 |
| 22 | CIN3 | .008 | .046 | .035 | 0 | .026 |
| 24 | +/− CIN | .029 | .277 | 0 | 0 | 0 |
| 26 | CIN2 | .030 | .368 | .220 | 0 | .153 |
| 27 | SC CANCER | .082 | .439 | 0 | 0 | .034 |
| 28 | N.D. | .142 | .071 | .037 | 0 | .008 |
| 30 | CIN1 | .038 | N.D. | .080 | 0 | .049 |
| 31 | NORMAL | .003 | .007 | .041 | .010 | .024 |
| 32 | NORMAL | .056 | .089 | .077 | .038 | .020 |
| 33 | GENITAL WART | .028 | .071 | 0 | 0 | .028 |
| 34 | CIN1 | .010 | .022 | .083 | 0 | .060 |
| 36 | CIN2 | .151 | .041 | .077 | .415 | .064 |
| 37 | +/− CIN | .088 | .104 | .073 | 0 | .058 |
| 38 | CIN2 | .040 | .495 | .010 | 0 | .218 |
| 39 | CIN2 | .006 | .304 | 0 | 0 | .047 |
| 40 | CIN2 | .032 | .301 | .017 | 0 | .006 |
| 42 | GENITAL WART | .030 | .108 | .043 | 0 | .017 |
| 43 | NORMAL | .011 | .026 | .003 | 0 | 0 |
| 44 | GENITAL WART | .011 | .064 | .036 | 0 | .023 |
| 45 | GENITAL WART | .018 | .040 | .030 | .007 | .021 |
| 47 | MONONUCLEOSIS | .004 | .071 | .043 | 0 | .037 |
| 54 | SC CANCER | .064 | .384 | 0 | 0 | .036 |
| 61 | UVI | .037 | .569 | .297 | 0 | .168 |
| 62 | GLAUCOMA | 0 | .084 | .041 | 0 | 0 |
| 63 | N.D. | .052 | .198 | .035 | 0 | .038 |
| 64 | CONVULSIONS | 0 | .189 | 0 | 0 | 0 |
| 65 | N.D. | .003 | .050 | .031 | 0 | .068 |
| 66 | CIN1 | .009 | .026 | .046 | 0 | .028 |
| 67 | CIN1 | .059 | .267 | .001 | 0 | .018 |

TABLE 11-continued

Type-Specific Detection Of
I$_g$A In HPV-Infected Patient Antisera

| Patient Number | Histology[1] | HPV Type Specific Polypeptide | | | | |
|---|---|---|---|---|---|---|
| | | PV[2] | 16[3] | 6[4] | 18[5] | 33[6] |
| 68 | N.D. | .011 | .060 | .039 | 0 | .029 |
| 69 | N.D. | 0 | .030 | .050 | 0 | .056 |
| 70 | CIN2 | .021 | .030 | .043 | 0 | .043 |
| 71 | VAGINAL WARTS | .016 | .029 | .052 | 0 | .029 |
| 72 | +/− CIN | .086 | .066 | .076 | 0 | .025 |
| 73 | N.D. | .038 | .059 | .045 | 0 | .037 |
| 74 | NORMAL | .002 | .017 | .066 | 0 | .042 |
| 75 | METAPLASIA | .042 | .096 | .265 | .0001 | .115 |
| 76 | CIN 2-3 | .020 | .070 | .058 | 0 | .030 |
| 77 | CIN1 | 0 | .022 | 0 | 0 | .046 |
| 78 | CIN2 | .004 | .040 | .035 | 0 | .080 |
| 79 | AUTOIMMUNE DISEASE | .013 | .454 | 0 | 0 | 0 |
| 80 | WRIST FIX | 0 | .238 | 0 | 0 | .017 |
| 81 | N.D. | .022 | .219 | .026 | .004 | .058 |
| 82 | JUVENILE DIABETES | 0.009 | .346 | 0 | .007 | 0 |
| 83 | MIGRAINE | 0 | .131 | 0 | .026 | 0 |
| 84 | SINUITIS | .027 | .315 | 0 | 0 | 0 |
| 85 | N.D. | 0 | .035 | .012 | 0 | .040 |
| 86 | N.D. | .640 | .364 | 0 | 0 | 0 |
| 87 | N.D. | .014 | .069 | .040 | 0 | .061 |
| 88 | N.D. | .019 | .067 | 0.028 | 0 | .038 |
| 89 | N.D. | .028 | .056 | .029 | 0 | .022 |
| 90 | N.D. | .007 | .086 | .035 | 0 | .057 |
| 91 | N.D. | .002 | .100 | .039 | 0 | .023 |
| 92 | N.D. | .067 | .106 | .720 | 0 | .032 |
| 93 | N.D. | .045 | .052 | .132 | 0 | .054 |
| 94 | N.D. | .031 | .082 | .076 | 0 | .054 |

[1]Histology is reported for each antisera donor as in note 2 to Table 10.
[2]PV is control papilloma virions isolated from moose warts.
[3]"16" indicates polypeptide 245 was included in the well having a sequence deduced from HPV type 16.
[4]"6" indicates polypeptide K70 was included in the well and having a sequence deduced from HPV type 6.
[5]"18" indicates polypeptide K69 was included in the well and having a sequence deduced from HPV type 18.
[6]"33" indicates polypeptide K72 was included in the well having a sequence deduced from HPV type 33.

The results in Table 11 show that patients harboring various latent HPV infections contain in their blood immunoglobulin IgA antibody molecules that immunoreact preferentially with one over another HPV type-related polypeptide. For example, patient 1 is a confirmed HPV type 16 infected individual, as determined using ViraType DNA Typing Kit (Molecular Diagnostics, Gaithersburg, Md.), and his blood contained IgA antibody molecules that immunoreact substantially with HPV type 16-related polypeptide 245, and immunoreacted only to a small degree with type 33-related polypeptide K72. Patient 36 contained in his blood IgA antibody molecules that preferentially immunoreact with HPV type 18-related polypeptide K69. Patients 75 and 92 contained in their blood IgA antibody molecules preferentially immunoreacting with HPV type 6-related polypeptide K70.

The results in Table 11 demonstrate one embodiment of the present invention in which HPV related-polypeptides, whose amino acid residue sequences are deduced from different HPV types, can be used to detect and distinguish, in a type specific manner, antibody molecules that are induced by one HPV type but not another. HPV-related type specific polypeptides can be included in separate wells of the practiced ELISA assay or diagnostic kit, as above, or can be combined together and adsorbed onto a single solid support, such as in a single well.

A similar assay was conducted using labeled antibody conjugates to detect both IgA and IgG immunoglobulins in a panel of donor antisera. In that assay, the results were first obtained as above for antisera containing immunoglubulin IgA antibody molecules that immunoreacted with the HPV type specific polypeptides shown in Table 12.

Thereafter a similar ELISA assay was run on the same panel of antisera except using 50 ul of a solution containing horseradish peroxidase labeled polyclonal anti-human immunoglobulin IgG conjugate (Dakopatts) diluted 1:800 in NHS buffer in place of the IgA conjugate. After formation of a second immunoreaction product, and then rinsing as before, 50 ul of an ABTS substrate solution (ABTS at a concentration of 0.2 mg per ml of 0.002M Citrate, pH 5.0, 0.009% hydrogen peroxide) was admixed into each well to form a color developing-reaction admixture. After maintaining the developing-reaction admixture in the dark for 20 minutes at room temperature, the O.D. of the solution admixture was measured using a multiskan plate reader equipped with a 415 nm filter.

The results of detecting both IgA and IgG antibody molecules in human donor blood that immunoreact with HPV-related polypeptides is shown in Table 12, with the same headings as for Table 11.

TABLE 12

Type-Specific Detection Of I$_g$A and I$_g$G In HPV-Infected Patient Antisera

| Patient Number | PV | | 16 | | 6 | | 18 | | 33 | |
|---|---|---|---|---|---|---|---|---|---|---|
| | I$_g$A | I$_g$G | I$_g$A | I$_g$G | I$_g$A | I$_g$G | I$_g$A | I$_g$G | I$_g$A | I$_g$G |
| 1 | .034 | 0 | .012 | 0 | .106 | .345 | .013 | .007 | .062 | .192 |

TABLE 12-continued

| Patient Number | Type-Specific Detection Of I$_g$A and I$_g$G In HPV-Infected Patient Antisera | | | | | | | | | |
|---|---|---|---|---|---|---|---|---|---|---|
| | PV | | 16 | | 6 | | 18 | | 33 | |
| | I$_g$A | I$_g$G | I$_g$A | I$_g$G | I$_g$A | I$_g$G | I$_g$A | I$_g$G | I$_g$A | I$_g$G |
| 2 | .035 | 0 | .053 | .046 | .082 | .202 | .001 | .038 | .038 | .247 |
| 3 | .027 | .034 | .048 | .239 | .063 | .247 | .004 | .117 | .025 | .384 |
| 4 | .000 | .032 | .294 | .156 | .304 | .286 | 0 | .032 | .085 | .248 |
| 5 | .067 | .192 | .122 | .789 | .112 | .360 | .001 | .160 | .084 | .586 |
| 6 | .014 | 0 | .066 | .374 | .086 | .626 | 0 | 0 | .095 | .389 |
| 7 | .152 | .407 | .253 | .654 | .093 | 1.009 | 0 | 0 | .042 | .527 |
| 8 | .054 | .275 | .619 | .367 | .112 | 1.101 | .368 | .210 | .075 | .556 |
| 9 | 0 | 0 | .048 | .117 | .024 | 1.494 | 0 | .326 | .086 | .394 |
| 10 | .024 | 0 | .034 | .064 | .054 | .192 | 0 | 0 | .054 | .233 |
| 11 | .045 | 0 | .123 | .064 | .033 | .442 | 0 | .114 | .058 | .374 |
| 12 | .031 | 0 | .082 | .196 | .089 | .376 | 0 | .192 | .061 | .748 |
| 13 | .032 | 0 | .181 | .119 | .152 | .215 | 0 | 0 | .098 | .207 |
| 14 | 0 | .080 | .370 | .274 | 0 | .019 | 0 | 0 | .043 | .438 |
| 15 | .019 | .056 | .018 | .520 | .029 | .520 | .006 | .107 | .014 | .520 |
| 16 | .070 | 0 | .103 | .220 | .122 | .048 | 0 | 0 | .106 | .106 |
| 17 | .040 | 0 | .020 | 0 | 0 | .074 | 0 | 0 | 0 | 0 |
| 18 | .065 | .069 | 0 | N.D. | .092 | .117 | 0 | 0 | .048 | .051 |
| 19 | 0 | .029 | .162 | .093 | .607 | .201 | 0 | 0 | .105 | .209 |
| 20 | 0 | N.D | .055 | .578 | .104 | .818 | 0 | 0 | .020 | 0.009 |
| 21 | .044 | 0 | .052 | 0 | .073 | 0 | 0 | 0 | .071 | 0 |
| 22 | .032 | .060 | 0 | .051 | .052 | .549 | .020 | .036 | .038 | .286 |
| 23 | .023 | .089 | .056 | .311 | .016 | .555 | 0 | 1.456 | .029 | .209 |
| 24 | .041 | .861 | .046 | 1.056 | .012 | 0 | 0 | 0 | .046 | 0 |
| 25 | .031 | 0 | .032 | .007 | .123 | .094 | .012 | 0 | .035 | .138 |
| 26 | .150 | .442 | .177 | .568 | .297 | 1.900 | .161 | .766 | .265 | .982 |
| 27 | .380 | .378 | .284 | .886 | 0 | 0 | 0 | 0 | 0 | 0 |

15. Polypeptide Ligand Affinity Isolation of Anti-HPV Latent Protein Antibody Molecules From Human Blood Ten mg of polypeptide 245, prepared as described in Example 1, were dissolved in water and subsequently coupled to 4 ml of packed CH-Sepharose beads (Pharmacia) according to the manufacturer's instructions to form a polypeptide 245-agarose solid support. The prepared support was first washed with 10 mls of 4 M KSCN, then washed with 400 mls of PBS to form an equilibrated 245-support. A second support was similarly prepared using a control polypeptide that had no sequence homology to HPV E region ORFs to form an equilibrated control support.

Antisera from a CIN patient having antibody molecules immunoreactive with polypeptide 245, as determined using the procedure described in Example 9, were collected. Two mls of the collected antisera was applied at a flow rate of 5 ml per hour to the control support, and the eluant off of the support was collected. Thereafter the collected eluant was similarly applied to the equilibrated 245-support and the support was then washed with about 80 mls of PBS containing 0.5M NaCl to rinse off any material that was not specifically immunoreacted with the polypeptide contained on the 245-support.

Immunoreacted antibody molecules were then eluted off of the 245-support by adding 4M KSCN at a flow rate of 5 ml per hour to the support, and collecting the eluant in fractions. The O.D. of the fractions was measured at 280 nm, the peak-containing fractions were determined and pooled to yield an antibody-containing pool. The pool was then dialysed against PBS to yield a solution containing polypeptide 245-isolated purified human anti-HPV latent protein antibody molecules. The antibody molecules contained in the solution so prepared are referred to as affinity purified or affinity isolated human anti-HPV latent protein antibody molecules.

The resulting affinity isolated antibody molecules represents a substantially isolated antibody because greater than 50% of the antibody molecules contained in the solution have the capacity to immunoreact with a HPV type 16-related polypeptide. As demonstrated herein, these antibody molecules also have the capacity to immunoreact with a HPV latent protein.

16. Detection of Nuclear HPV Latent Proteins Using Human Anti-HPV Latent Protein Antibody Molecules
  a. Western Immunoblotting The cell line NIH3T3/HPV16 is a mouse fibroblast NIH3T3 cell line stably transected with HPV type 16 (Yasumoto it al., *J. Virol.*, 57:572–577, 1986), and was obtained from Dr. J. DiPaolo. C4II is a HPV type 18-carrying cervical carcinoma cell line (Yee et al., *Am. J. Pathol.*, 119:361–366,1985), and was obtained from the ATCC and cultured according to ATCC specifications.

The cell lines HT-3, CaSki and SiHa, described in Example 5, NIH3T3/HPV16 and C4II, and the normal cell line NIH3T3 (ATCC) were subjected to Western immunoblot assay as described in Example 5, with the exceptions as noted.

Cell lysates were subjected to SDS-PAGE as before, but using 7% polyacrylamide gels and the molecular weight marker proteins indicated in the legend to FIG. 5. After transfer of the electrophoresed cell lysates to nitrocellulose and blocking, the blocked blots were maintained for 12 hours in (a) a solution of polypeptide 245-affinity isolated human anti-HPV latent protein antibody molecules, prepared in Example 15 and diluted 1:10 in BLOTTO, (b) undiluted culture supernatant from hybridoma 245:11E3 prepared as in Example 6b, or (c) a solution containing rabbit affinity isolated anti-polypeptide 245 antibody molecules prepared in Example 4 and diluted 1:32 in BLOTTO to allow an immunoreaction product to form between the admixed antibody compositions and the latent papillomavirus proteins present as a solid phase on the blots.

The washed blots were then maintained in BLOTTO containing alkaline phosphatase conjugated to either (a) anti-human IgA, (b) anti-mouse IgG, or (c) anti-rabbit IgG, respectively, each diluted 1:1000, to allow a second immunoreaction product to form between the second admixed antibody and the first formed immunoreaction product present on the solid phase of the blot. The blots were then washed and the solid phase immunoreaction products were visualized using the chromogenic substrate developer solution for the developing times indicated in the legend to FIG. 5.

Results using the Western immunoblot assay to detect latent papillomavirus proteins with human antibody molecules are shown in FIG. 5.

For instance, the human antibody molecules immunoreacted with a 48 kd protein in C4II cells, with a 48 kd and 26 kd protein in NIH3T3/HPV16 cells, and with a 58 kd protein in CaSki cells on long exposure (left portion of FIG. 5A), but no immunoreaction was seen with control cells HT-3 or NIH3T3.

As a further characterization, monoclonal antibody 245:11E3 immunoreacted with the 58 kd protein in CaSki cells but not in HT-3 of SiHa cells (FIG. 5B). The affinity isolated rabbit antibody immunoreacted predominantly with the 48 kd protein, and minimally with the 51 kd and 58 kd proteins in CaSki cells (FIG. 5C).

b. Immunohistochemical Detection CaSki, C-33A, HT-3, SiHa and Hela

Tissue culture cells were prepared for immunochistochemical detection as described in Example 8a except that the fixed cells were blocked in 8% NHS for 30 minutes and were immunoreacted for 90 minutes using a solution containing either (a) polypeptide 245-affinity isolated human anti-HPV latent protein antibody molecules, prepared in Example 15 and diluted 1:5 in BLOTTO, or (b) antibody molecules present in a supernatant from hybridoma 245:11AE3 culture,prepared in Example 6b and diluted 1:18 in BLOTTO. The results showed that both antibody molecules immunoreacted with HPV type 16-infected CaSki cell but did not immunoreact with the other cell lines tested. Visualized immunoreaction product in CaSki cells showed strong staining in the cell nucleus. The nuclear localization was confirmed by subcellular fractionation of CaSki cells to isolate the nuclei, and subsequent analysis of the isolated nuclei to identify a 58 kd protein by Western immunoblotting according to Example 16a.

These analyses indicate that both the human and the mouse polypeptide 245-affinity isolated antibody molecules immunoreacted with a nuclear HPV latent 58 kd protein and also with a 26 kd and 48 kd HPV latent protein.

17. Correlation of Dysplasia Severity With IgA Anti-HPV Latent Protein Antibody

Molecules in Human BloodyStatistical analysis was performed on ELISA immunoreaction results obtained by the ELISA assay in Example 9, using the antisera samples obtained from patients having dysplasias hystologically confirmed as CINI, CIN2 or CIN3 as defined in note 2 to Table 10. Table 13 shows the results of the statistical analysis.

TABLE 13

| CIN Severity | Sample Size | Mean OD 492 | Standard Deviation |
|---|---|---|---|
| CIN1 | 32 | 0.137 | 0.198 |
| CIN2 | 20 | 0.162 | 0.126 |
| CIN3 | 14 | 0.320 | 0.174 |

[1]OD at 492 nm was measured by immunoreaction of patient IgA antibody molecules with polypeptide 245 in ELISA assay.

The results show a correlation between dysplasia severity and anti-HPV latent protein antibody immunoreactivity with polypeptide 245. Therefore, the present methods and diagnostic systems for detecting anti-papillomavrus latent protein antibody molecules can be utilized to correlate patient IgA immunoreactivity and titers with the severity of papillomavirus induced genital lesions and dysplasia.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A polypeptide represented by a formula selected from the group consisting of:

MADPAGTNGEEGTGC,

HEDEDKENDGDSLPTC,

RPFKSNKSTCC,

CCDWCIAAFGLTPSI,

TYDSEWQRDQFLSQVKIPC,

HKSAIVTLTYDSEWQRDQC, and

CINCQKPLCPEEKQRH.

2. A polypeptide having an amino acid residue sequence represented by the formula selected from the group consisting of:

SSTWHWTGHNVKHKSAIVTLTYD,
HKSAIVTLTYDSEWQRDC,
HKSAIVTLTYDSEWQRC,
HKSAIVTLTYDSEWQC,
HKSAIVTLTYDSEWC,
HKSAIVTLTYDSEC,
HKSAIVTLTYDSC,
HKSAIVTLTYDC,
HKSAIVTLTYC,
KSAIVTLTYDSEWQRDC,
SAIVTLTYDSEWQRDC,
AIVTLTYDSEWQRDC,
IVTLTYDSEWQRDC,
VTLTYDSEWQRDC,
TLTYDSEWQRDC, and
LTYDSEWQRDC.

3. A composition comprising a substantially pure human papillomavirus 54 kd filamentous protein, said protein containing a first epitope having the capacity to immunoreact with anti-polypeptide antibodies induced by a polypeptide represented by the formula:

MADPAGTNGEEGTGC;

and containing a second epitope having the capacity to immunoreact with anti-polypeptide antibodies induced by a polypeptide represented by the formula:

CINCQKPLCPEEKQRH.

4. A composition comprising a substantially pure human papillomavirus 48 kd filamentous protein, said protein containing a first epitope having the capacity to immunoreact with anti-polypeptide antibodies induced by a polypeptide represented by the formula:

MADPAGTNGEEGTGC;

and containing a second epitope having the capacity to immunoreact with anti-polypeptide antibodies induced by a polypeptide represented by the formula:

CINCQKPLCPEEKQRH.

5. A composition comprising a substantially pure human papillomavirus 112 kd diffuse protein, said protein containing a first epitope having the capacity to immunoreact with anti-peptide antibodies induced by a polypeptide represented by the formula:

HEDEDKENDGDSLPTC;

and containing a second epitope having the capacity to immunoreact with anti-polypeptide antibodies induced by a polypeptide represented by the formula:

HKSAIVTLTYDSEWQRDQC.

6. A composition comprising a substantially pure human papillomavirus 51 kd nuclear protein, said protein containing an epitope having the capacity to immunoreact with anti-peptide antibodies induced by a polypeptide represented by the formula:

HKSAIVTLTYDSEWQRDQC.

7. A diagnostic system, in kit form, comprising a package containing, in an amount sufficient to perform at least one assay, a substantially pure human papillomavirus latent protein selected from the group consisting of:
  i) the 112 kd diffuse protein,
  ii) the 54 kd filamentous protein,
  iii) the 48 kd filamentous protein,
  iv) the 51 kd nuclear protein; and
  v) the 58 kd nuclear protein.

* * * * *